(12) United States Patent
Wakizaka et al.

(10) Patent No.: US 9,364,147 B2
(45) Date of Patent: Jun. 14, 2016

(54) SYSTEM, METHOD AND DEVICE FOR AUTOMATIC NONINVASIVE SCREENING FOR DIABETES AND PRE-DIABETES

(71) Applicant: LIFELENS, LLC, Santa Monica, CA (US)

(72) Inventors: Jason Wakizaka, Los Angeles, CA (US); Wilson To, Bellevue, WA (US); Tade Souaiaia, Los Angeles, CA (US)

(\*) Notice: Subject to any disclaimer, the term of this patent is extended or adjusted under 35 U.S.C. 154(b) by 0 days.

(21) Appl. No.: 14/178,163

(22) Filed: Feb. 11, 2014

(65) Prior Publication Data

US 2014/0228668 A1    Aug. 14, 2014

Related U.S. Application Data

(60) Provisional application No. 61/843,512, filed on Jul. 8, 2013, provisional application No. 61/763,287, filed on Feb. 11, 2013.

(51) Int. Cl.
*A61B 5/00* (2006.01)
*A61B 3/14* (2006.01)
*A61B 5/026* (2006.01)
*A61B 3/12* (2006.01)
*A61B 5/02* (2006.01)

(52) U.S. Cl.
CPC ... *A61B 3/14* (2013.01); *A61B 3/12* (2013.01); *A61B 5/02007* (2013.01); *A61B 5/0261* (2013.01); *A61B 5/7275* (2013.01); *A61B 5/489* (2013.01)

(58) Field of Classification Search
CPC ........ A61B 3/12; A61B 3/14; A61B 5/02007; A61B 5/0261; A61B 5/489; A61B 5/7275; A61B 3/152
See application file for complete search history.

(56) References Cited

U.S. PATENT DOCUMENTS

| 5,815,242 | A | * | 9/1998 | Anderson et al. | 351/221 |
|---|---|---|---|---|---|
| 6,702,806 | B2 | * | 3/2004 | Gray et al. | 606/5 |
| 6,830,336 | B2 | * | 12/2004 | Fransen | 351/246 |
| 7,774,036 | B2 | * | 8/2010 | Halldorsson et al. | 600/323 |
| 8,109,633 | B2 | * | 2/2012 | Molnar et al. | 351/206 |
| 8,229,177 | B2 | * | 7/2012 | Duffy et al. | 382/115 |
| 8,801,183 | B2 | * | 8/2014 | Shahidi | A61B 3/1241 351/206 |
| 8,836,778 | B2 | * | 9/2014 | Ignatovich et al. | 348/78 |
| 8,896,682 | B2 | * | 11/2014 | Bressler et al. | 348/78 |
| 2009/0143685 | A1 | * | 6/2009 | Elner et al. | 600/476 |
| 2011/0169935 | A1 | * | 7/2011 | Henriksen | 348/78 |

OTHER PUBLICATIONS

To WJ et al. "Correlation of conjunctival microangiopathy with retinopathy in type-2 diabetes mellitus (T2DM) patients." Clinical hemorheology and microcirculation 47: pp. 131-141 (2011).*

\* cited by examiner

*Primary Examiner* — Amanda Lauritzen Moher
(74) *Attorney, Agent, or Firm* — Karish & Bjorgum, PC

(57) ABSTRACT

A system for an automatic noninvasive screening for diabetes and pre-diabetes using a device to take at least one image of a patient's eye, executing non-transitory instructions executable on a processor for analyzing the image and displaying an indication if the patient has diabetes.

22 Claims, 34 Drawing Sheets

| Priority Group | Microangiopathy | Scientific Basis | Observational Description |
|---|---|---|---|
| A | abnormal vessel diameter | Vessel wall response to accommodate increased shearing forces | Above average thickness in cross sectional distance of vessel diameter |
| A | vessel tortuosity | Vessel wall response to accommodate increased systemic pressure | Meandering, sinusoidal spanning across conjunctiva |
| A | uneven vessel thickness | Tortuousity + rifts cause additional damage to specific areas of vessel wall | Beading of vessels; often nodular spanning across segments |
| A | damaged vessel | Ruptures often from microaneurysms | Disruptions in the vessel wall, flaring from the wall, often localized hemosiderin |
| A | microaneurysm | Occlusion due to increase in adhesion molecule expression in micro vessels | Nodules that develop in the loops of tortuous vessels, and bulbular in vessel ends |
| B | abnormal vessel distribution | Many causes, can stem from various cues | Vessels should be evenly distributed throughout the conjunctiva |
| B | blood flow sludging | Cell adhesion changes and minor vessel occlusions | Clumping, slow flow through arterioles and venules |
| B | ischemic sites | Death of vessels in localized vicinity | Absence of both arteriolar and venular vessels in area |
| B | abnormal Arteriole:Venule ratio | Angiogenesis or death of blood vessels | Unequal arteriolar: venular concentrations |
| B | hemosiderin deposits | Result of damage and leakage of blood into sclera - oxidation of heme group | Brown, nebulous areas in the conjunctiva |
| B | abnormal blood flow velocity | Shear force and stress change responses | Faster or slower than normal blood flow (not blood cell velocity) |
| C | distended vessel | Occlusions | Vessels become thinner, then disappearing |
| C | "boxcar" blood flow phenomena (trickled flow) | Occlusions upstream of flow due to changes in vessel diameter | Patterned trickling of blood cells (boxcar effect) in conjunctival regions |
| C | comma sign | To be discovered | Short vessel extensions stemming transectional to vessel |

Figure 26

SYSTEM, METHOD AND DEVICE FOR AUTOMATIC NONINVASIVE SCREENING FOR DIABETES AND PRE-DIABETES

CROSS-REFERENCE TO RELATED APPLICATIONS

This application claims the benefit under 35 U.S.C. §119 (e) of U.S. Provisional Patent Application Ser. No. 61/763,287, filed on Feb. 11, 2013, and of U.S. Provisional Patent Application Ser. No. 61/843,512, filed on Jul. 8, 2013, the contents of which are incorporated herein by reference in their entirety.

FIELD OF THE INVENTION

The present invention relates to diabetes and pre-diabetes screening, more specifically to a system, method and device for automatic noninvasive screening for diabetes and pre-diabetes.

BACKGROUND

Diabetes is a killer around the world. Currently, in United States, according to National Institutes of Health statistics: Diabetes affects 25.8 million or 8.3% of the U.S. population. Pre-diabetes conditions exist in 79 million or 35% of the adult population. The total annual health care cost for treatment is $174 billion. United Health Group projects that by 2020, in the US only 15% of the adult population will have diabetes; 37% of the adult population will be have pre-diabetes condition; and the total annual health care cost related to both will be nearly $500 billion. As can be seen, there is a great need to be able to reduce the numbers of diabetes and pre-diabetes cases. Detection and prevention are the best ways to combat these diseases.

There are many different methods of screening for diabetes and pre-diabetes in existence today. These methods include:
1) HbA1c blood test—Blood is drawn, and tested for levels of HbA1c
    <=5%=normal; 5.7%-6.4%=pre-diabetes; >6.5%=diabetes
2) Fasting Plasma Glucose Test—patient fasts for 8 hours, then blood is tested for glucose levels—requires a second test to confirm
    <=99 mg/dL=normal; 100-125=pre-diabetes; 126+=diabetes
3) Oral Glucose Tolerance Test—patient fasts for 8 hours, then drinks 75 g glucose dissolved in water, 2 hours later blood is tested for glucose levels.
    <=139 mg/dL=normal; 140-199=pre-diabetes; 200+=diabetes.

Additionally, new devices are being developed, such as for example, the Veralight SCOUT DS, which is a noninvasive, table-top screening device that shines a light on a patient's arm and measures the reflected light.

Disadvantageously, the current art requires invasive methods to draw blood from a patient. Also, the patient must fast for the test results to be accurate. Further, the drawn blood must be sent to a lab, which involves extra time, extra cost, a higher risk of blood spoilage and or bad results due to errors in documentation or transfer. Finally, the patient must go to a physician to have these tests completed. There is no current available home-based test to determine if patient has diabetes or pre-diabetes conditions.

Therefore, there is a need for noninvasive, fast and convenient device for automatic noninvasive screening for diabetes and pre-diabetes.

SUMMARY

The invention is a system for an automatic noninvasive screening for diabetes and pre-diabetes by using at least one image. The system has an imaging device for taking at least one image of a patient's eye, a processor, and an indicator.

The processor is operably connected to the imaging device and has non-transitory instructions executable on the processor for analyzing the image. The indicator is operably connected to the imaging device and the processor and displays an indication if the patient has diabetes. In one embodiment of the system, the imaging device and the processor can be contained in a self-contained unit. Optionally, the imaging device and the processor can be separate units that are communicatively coupled to each other.

The non-transitory instructions executable on the processor can comprise instructions for screening the at least one image for diabetes and pre-diabetes. The system can further comprise non-transitory instructions executable on the processor to perform image processing algorithms to detect the presence, and measure when appropriate, abnormalities in the microcirculation of the patient.

The abnormalities can be assigned three levels of importance. The abnormalities in the highest importance level can be selected from the group consisting of abnormal vessel diameter, vessel tortuosity, uneven vessel thickness, damaged vessel, and microaneurysms. The abnormalities in the second importance level can be selected from the group consisting of abnormal vessel distribution, blood flow sludging, ischemic sites, abnormal Arteriole, Venule ratio, hemosiderin deposits, and abnormal blood flow velocity. The abnormalities in the third importance level can be selected from the group consisting of abnormal morphology, distended vessel, "boxcar" blood flow phenomena (trickled flow), and comma sign.

The current invention is also a method for automatic noninvasive screening for diabetes and pre-diabetes by using at least one image. The method comprises the steps of taking at least one image of a patient's eye using the imaging device described above, storing the at least one image in a storage for processing, determining if more than one image is to be processed, analyzing the at least one image, calculating a risk profile for the patient based upon the at least one image, and determining if the patient has diabetes.

The method can also include the step of registering a plurality of images to form a single image if the determination is made that there is more than one image. The calculated risk profile can determine if the patient is pre-diabetic.

The step of analyzing the at least one image can comprises the steps of detecting hemosiderin deposits, detecting venuoles, determining an arteriole to venuole ratio, determining venuole midpoints, determining the venuole midpoint diameters and angles, detecting venuole paths by clustering the venuole midpoints, detecting abnormalities, detecting boxcar flow in the blood vessels, detecting ischemic sites, and detecting abnormal blood vessel distribution. The abnormalities detected can comprise tortuosity, uneven thickness, damaged vessels, microaneurysms, distended vessels, and sickle vessels.

The venuole diameters and angles can be calculated using the steps of loading pixel values into a matrix, subdividing the image of the venuole diameters and angles into subsets, making microangiopathy priority groupings for each subsection analyzed, and determining a risk factor for the patient based on one or more of the priority groupings alone or in combination.

Additionally, the detection of venuoles can comprise the steps of creating a binary matrix with the same dimensions as the original image, determining for each pixel in the image, if the pixel is in the appropriate blood vessel color range and whether it exceeds a darkness intensity threshold, a color intensity threshold or both a darkness and a color intensity threshold, setting the corresponding bit in the matrix to true, otherwise set it to false if the threshold of step 2) is true, storing in a storage a position of the pixel corresponding to the true bit position in the matrix as an identified venuole, and creating an image mask from the matrix and the stored pixel information to isolate the venuoles identified in steps 1)-4).

The current invention is also a device useful for a system for automatic noninvasive screening for diabetes and pre-diabetes. The device has an eyepiece, a tube, a light source, a magnifying lens and a camera body. The tube has a proximal and distal end and an exterior and interior portion, and the eyepiece is attached to the distal end of the tube. The light source is affixed to the interior portion of the tube and the magnifying lens is affixed to the interior portion near the proximal end of the tube. The camera body is affixed to the proximal end of the tube.

The camera body can have an interior and exterior portion. The interior portion of camera body can have a camera sensor, a microprocessor connected to the camera sensor, and a storage for storing images connected to the microprocessor.

The device can also have a touchscreen affixed to the camera body opposite to the tube. The device can also have a hardware communications port, a wireless transmitter, or both a hardware communications port and a wireless transmitter for downloading the images from the storage in the device to an external storage, an archival repository or both an external storage and an archival repository. The device can also have a wired trigger, a wireless trigger, or both a wired and wireless trigger for activating the device to take an image of a patient's eye to analyze the risk factors for diabetes or pre-diabetes.

In one embodiment of the device, the device can comprise a handheld computer, a camera body coupled to the handheld computer, and a lens with a light source wrapped around the lens coupled to the camera body. The light source can direct light to the eye in a uniform, diffuse manner, as well as minimize reflected glare. Optionally, the light source can be composed of a silicon tube with LED lights placed inside of the tube. The LED's can be directed radially out, away from the lens. The device can also have a fiber optic fixation light mounted on a post rotatable around the lens.

In one embodiment of the method, the method can comprise the steps of capturing a color image of a patient's eye, storing the image m a storage for processing, converting the color image to a grayscale image, applying a box blur filter to the grayscale image, applying a noise reduction filter the box blur image, normalizing the noise reduced image, increasing the range between white (conjunctiva) and black (blood vessel) pixels on the normalized image, applying a Gaussian Matched filter to the range increased image, scoring each pixel of the Gaussian Matched image on a likelihood of being in a blood vessel, calculating, for each of the scored pixels, the optimal orthogonal angle, rank segmenting the results, identifying the best identified blood vessel candidates from the segmented rankings using a threshold, calculating a midpoint for each segment, calculating midpoints for the rank segmented pixels, calculating blood vessel diameters associated with each midpoint, chaining each identified midpoint to the other identified midpoints, calculating a line that connects and traverses the blood vessel through the chained midpoints creating a line, and performing feature analysis on the blood vessel using statistics and the blood vessel chains to identify and measure features in the micro circulation to identified diabetic conditions.

Optionally, only the light intensity of each pixel is stored, rather than color data for the step of converting the color image to grayscale. Calculating the light intensity of each pixel can be done using the formula: Gray Value=0.114B+0.587G+0.299R, where: B=blue channel; G=green channel; R=red channel.

The image noise can be reduced by applying a box blur filter. Additionally, the box blur filter can comprise the steps of creating a new image, where each pixel in the new image is equal to the average value of the neighboring pixels in the original image, defining neighboring pixels as a box with length k centered on the pixel, and repeating step b) for a number of iterations. Optionally, the length k is in the range of 1 pixel to the number of pixels in the image. Optionally the length k is five pixels.

The step of normalization increases the dynamic range of the image, exaggerating the difference in pixel intensity between the pixels in a blood vessel and pixels not in a blood vessel. Optionally, normalization can comprise the steps of analyzing each pixel for a white value and a black value, setting the whitest pixel to white, and the darkest pixel to black, and scaling all other pixels accordingly. The step of scaling can use the formula pixel(x,y)=[(pixel(x,y)−min)/(max−min)]×255, where pixel(x,y)=an individual pixel. Optionally, min is the smallest (minimum pixel intensity) and max is the largest pixel value, respectively, in the entire image.

Optionally, the image can be split into smaller bins, where min is the smallest (minimum pixel intensity) and max is the largest pixel value, respectively, in the local bin.

Optionally, the image can be enhanced using a Gaussian Matched Filter. Enhancement can comprise the steps of analyzing, for every point P(x,y), in the image a line of pixels of some length centered on P(x,y), scoring how closely the pixel intensities match a Gaussian curve, with P(x,y) acting as the mean, repeating the scoring for a number of equidistant radials, centered on P(x,y), and storing the highest score and an angle that produced the high score for every point in the image. Optionally, the score can be calculated using twelve radials.

Additionally, the midpoint chaining can use the O'Brien Midpoint Chaining algorithm to chain adjacent midpoints together to create a line that traverses the center of a blood vessel.

The method of the feature analysis can comprise the steps of identifying vessel tortuosity, calculating an average, maximum, minimum, and variance of diameter for each chain to determine abnormal vessel diameter and uneven vessel thickness, analyzing chains that terminate at a point not near the edge of the image, identifying terminated chains as damaged blood vessels, analyzing the chains identified as damaged vessels for a significant increase in diameter, a circular shape or both an increase in diameter and a circular shape at the end of the chain, identifying the chains of damaged vessels as a microaneurysm, analyzing chains identified as a damaged vessel for distended blood vessel, where the chains have a significant decrease in diameter at the end of the chain, identifying the distended blood vessels, dividing the image into a number of equal size sections, analyzing the divided image for abnormal vessel distribution, analyzing the divided image for ischemic sites, analyzing the image for "Boxcar" blood flow phenomena. Optionally, the circular shape can be detected with a Hough transform. Optionally, an average diameter and variance over all chains can be calculated.

The method can also have the step of analyzing the original color image for significant areas of yellow-brown color indicating hemosiderin deposits. Additionally, the method can also have the step of calculating vessel tortuosity. Blood vessel tortuosity can be calculated as being equal to the curvature of the chain divided by the length of the chain. Blood vessel tortuosity can also be calculated as being equal to the sum of the dot products over the sum of the lengths. Blood vessel tortuosity can also be calculated using the formula:

$$\frac{\sum_{i=1}^{n-1} u_i \cdot u_{i+1}}{\sum_{i=1}^{n-1} |u_{i+1} - u_i|}$$

BRIEF DESCRIPTION OF THE DRAWINGS

These and other features, aspects and advantages of the present invention will become better understood with regard to the following description, appended claims, and accompanying figures where:

FIG. 26 is a table prioritizing various microangiopathy with visible indicators;

DETAILED DESCRIPTION

Figure 1:
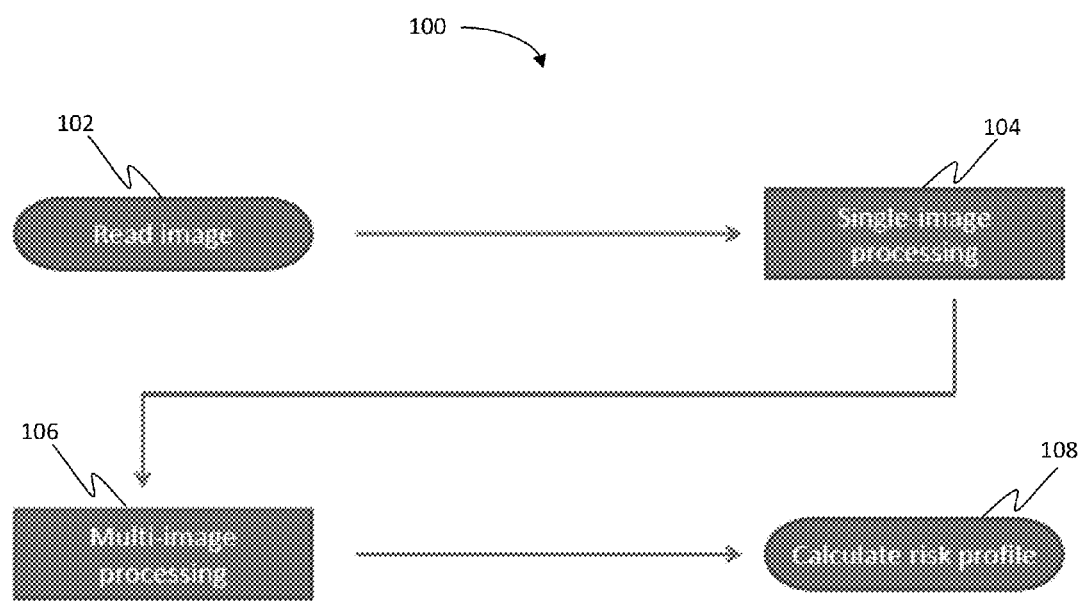
FIG. 1 is a basic flowchart diagram of a system for automatic noninvasive screening using a single image and multiple images for diabetes and pre-diabetes according to one embodiment.

The present invention overcomes the limitations of the prior art by providing a non-invasive, fast, inexpensive and accurate device that does not require any blood to be drawn, nor any lab analysis. The system can identify patients that are exhibiting traits that are consistent with early-stage development of diabetes. By identifying these at-risk patients in the pre-diabetes phase, years before the patient develops the full disease, the patient can reduce the risk of developing the disease by 58% according to the CDC/National Diabetes Prevention Program. The present invention is a fast, reliable means to reduce this disease.

As a patient goes from healthy, to pre-diabetic, to diabetic, levels of HbA1c in the body raise above healthy levels. This change in the composition of the red blood cells creates distinct and predictable changes in the morphology of the microcirculation. While these changes are systemic, occurring throughout the body, the bulbar conjunctiva provides a view of the microcirculation, allowing for external observation of the abnormalities. Using the present invention, no blood is drawn. Therefore reducing the risk and discomfort to the patient. Additionally, no additional personnel need to be trained to draw blood from the patient and the proper handling of blood. The risk of the passing of any blood born disease is eliminated.

The device is fast, providing results almost immediately, reducing the wait time for both the physician and the patient. The system uses computer vision based tests to determine diabetes or pre-diabetes conditions. Therefore, there is no chemical inventory or costs incurred by the physician. Only minimal incremental costs of exams are needed to perform the screening. Those result in lower costs for the patient, the physician, or any hospital or clinic providing these services. Additionally, the devices are small and portable. One device could easily cover one or more examination rooms due to the speed and efficiency of the device. Also, due to the portable nature of the device it is possible for clinicians in the field to provide quick and accurate determination of diabetes and pre-diabetes conditions. Currently, clinical studies are underway to match the specific structures identified by the device with a patient's HbA1c. The results will be incorporated into the device, and as more data is gathered the algorithms used in the device will be enhanced with information gathered over time.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any system, any device or part of a system or device disclosed in this disclosure will be determined by its intended use.

Methods and devices that implement the embodiments of the various features of the invention will now be described with reference to the drawings. The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment.

Throughout the drawings, reference numbers are re-used to indicate correspondence between referenced elements. In addition, the first digit of each reference number indicates the figure where the element first appears.

As used in this disclosure, except where the context requires otherwise, the term "comprise" and variations of the term, such as "comprising", "comprises" and "comprised" are not intended to exclude other additives, components, integers or steps.

In the following description, specific details are given to provide a thorough understanding of the embodiments. However, it will be understood by one of ordinary skill in the art that the embodiments may be practiced without these specific detail. Well-known circuits, structures and techniques may not be shown in detail in order not to obscure the embodiments. For example, circuits may be shown in block diagrams in order not to obscure the embodiments in unnecessary detail.

Also, it is noted that the embodiments may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be rearranged. A process is terminated when its operations are completed. A process may correspond to a method, a function, a procedure, a subroutine, a subprogram, etc. When a process corresponds to a function, its termination corresponds to a return of the function to the calling function or the main function.

Moreover, a storage may represent one or more devices for storing data, including read-only memory (ROM), random access memory (RAM), magnetic disk storage mediums, optical storage mediums, flash memory devices and/or other machine readable mediums for storing information. The term "machine readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, or a combination thereof. When implemented in software, firmware, middleware or microcode, the program code or code segments to perform the necessary tasks may be stored in a machine-readable medium such as a storage medium or other storage(s). One or more than one processor may perform the necessary tasks in series, distributed, concurrently or in parallel. A code segment may represent a procedure, a function, a subprogram, a program, a routine, a subroutine, a module, a software package, a class, or a combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted through a suitable means including memory sharing, message passing, token passing, network transmission, etc.

In the following description, certain terminology is used to describe certain features of one or more embodiments of the invention.

The term "arterioles" refers to blood vessels in the microcirculation that carry oxygenated blood to tissue.

The term "venuoles" refers to blood vessels in the microcirculation that carry deoxygenated blood away from the tissue.

The term "hemosiderin deposits" refers to iron deposits in the conjunctiva, outside of blood vessels, similar to a bruise.

Various embodiments provide a system, device and a method for an automatic noninvasive screening for diabetes and pre-diabetes. One embodiment of the present invention provides a system comprising one or more than one portable electronic device and one or more than one method for determining if a diabetes or pre-diabetes condition exists. The system, method and device will now be disclosed in detail.

Referring now to FIG. 1, there is a basic flowchart diagram 100 of a system for automatic noninvasive screening using a single image and multiple images for diabetes and pre-diabetes according to one embodiment. As can be seen, first an image is read from the device 102. Then, a determination is made to proceed 104 with either single-image processing or multi-image processing. Finally, an analysis is performed 106 to calculate the risk profile 108 of the patient based upon either the single-image processing or the multi-image processing.

Figure 2:
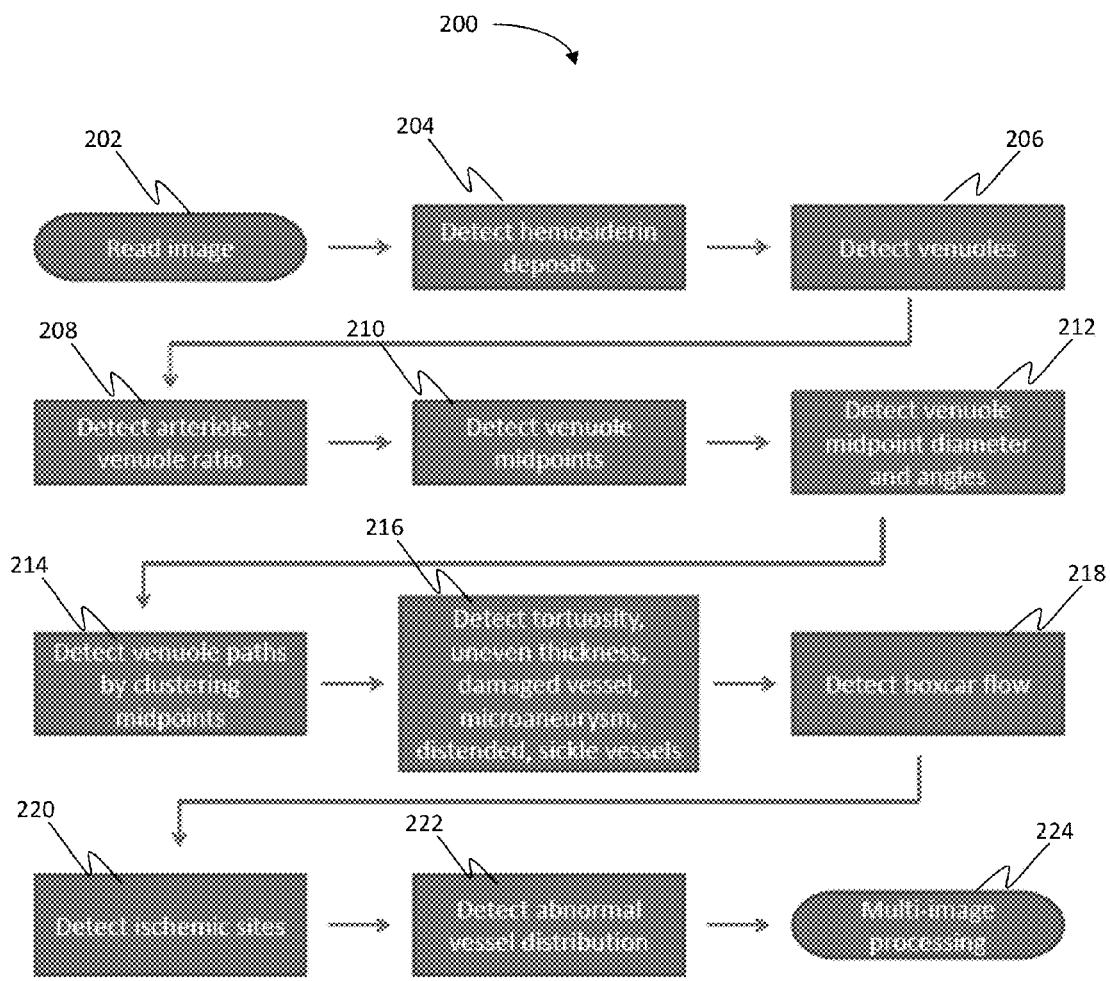
FIG. 2 is a is a detailed flowchart diagram of a system for automatic noninvasive screening for diabetes and pre-diabetes using a single image, according to one embodiment of the present invention.

Referring now to FIG. 2, there is shown a detailed flowchart diagram 200 of a system for an automatic noninvasive screening for diabetes and pre-diabetes using a single image, according to one embodiment of the present invention. As can be seen in this flowchart, a single image is read 202 from the device. Then, a variety of analysis is performed upon the single image. First, the image is analyzed to detect hemosiderin deposits 204. Next, the image is analyzed to detect venuoles 206. Next, the image is analyzed to determine an arteriole to venuole ratio 208. Then, the image is analyzed to determine venuole midpoints 210. Next, the image is analyzed to determine the venuole midpoint diameters and angles 212. Then, the image is analyzed to detect venuole paths 214 by clustering the midpoints. Next, the image is analyzed to detect virtuosity, uneven thickness, damaged vessels, microaneurysms, distended vessels, and sickle vessels. 216 Then, the image is analyzed to detect any boxcar flow 218 in the blood vessels. Next, the image is analyzed to detect ischemic sites 220. Finally, the image is analyzed to detect abnormal blood vessel distribution 222. Once all the single image analysis and detection has been performed then, multiple image processing 224 can begin.

Figure 3:
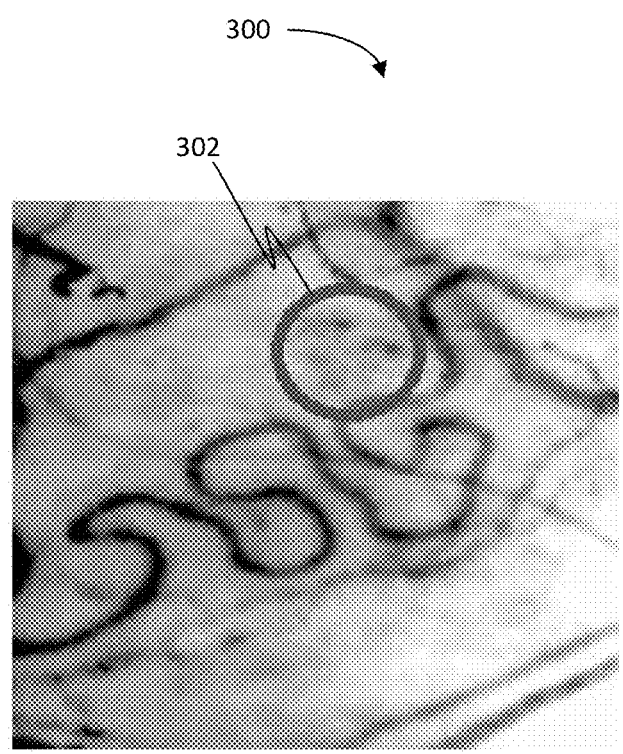
FIG. 3 is an image of hemosiderin deposits.

Referring now to FIG. 3, there is shown an image 300 of hemosiderin deposits. As can be seen, a circle 302 identifies a hemosiderin deposit in this image. Hemosiderin deposits are typically the remnants of a hemorrhage. The hemosiderin deposit area 302 typically presents a characteristic brown color. The system comprises non-transitory instructions executable on a microprocessor contained within the device for performing the steps of an algorithm that will detect any hemosiderin deposit contained in the image. Detection of hemosiderin deposit is accomplished by examining the image for significantly large areas that contains this characteristic color. In one embodiment, the algorithm uses a binary (i.e. true or false) indication that the image either does, or does not contain hemosiderin deposits.

Figure 4:
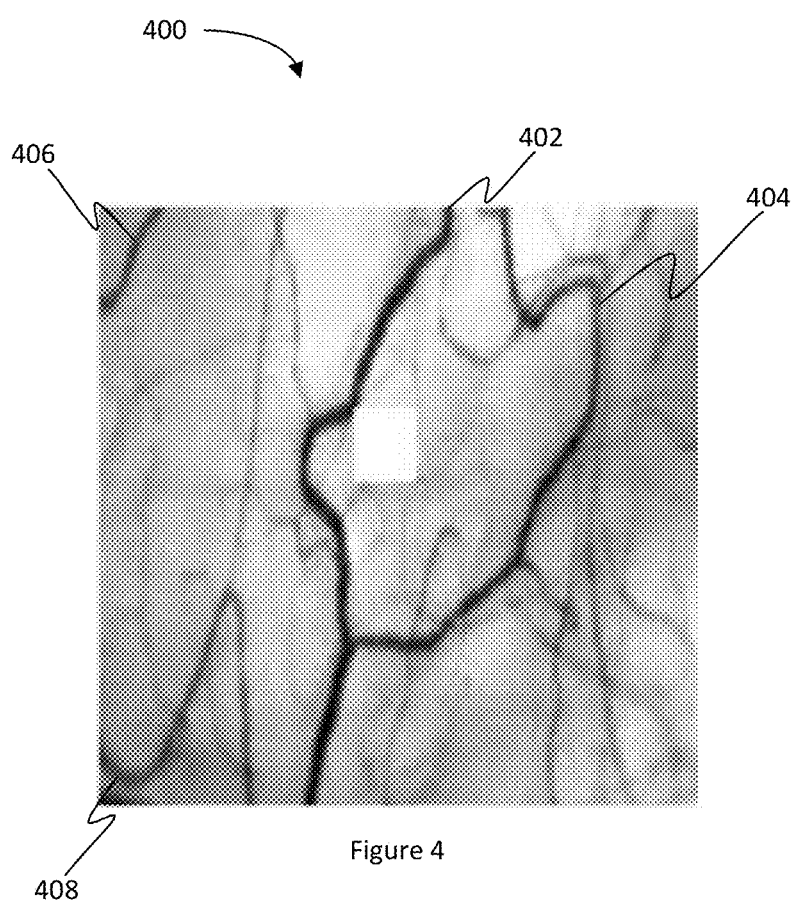
FIG. 4 is an image of venuoles.
Figure 5:
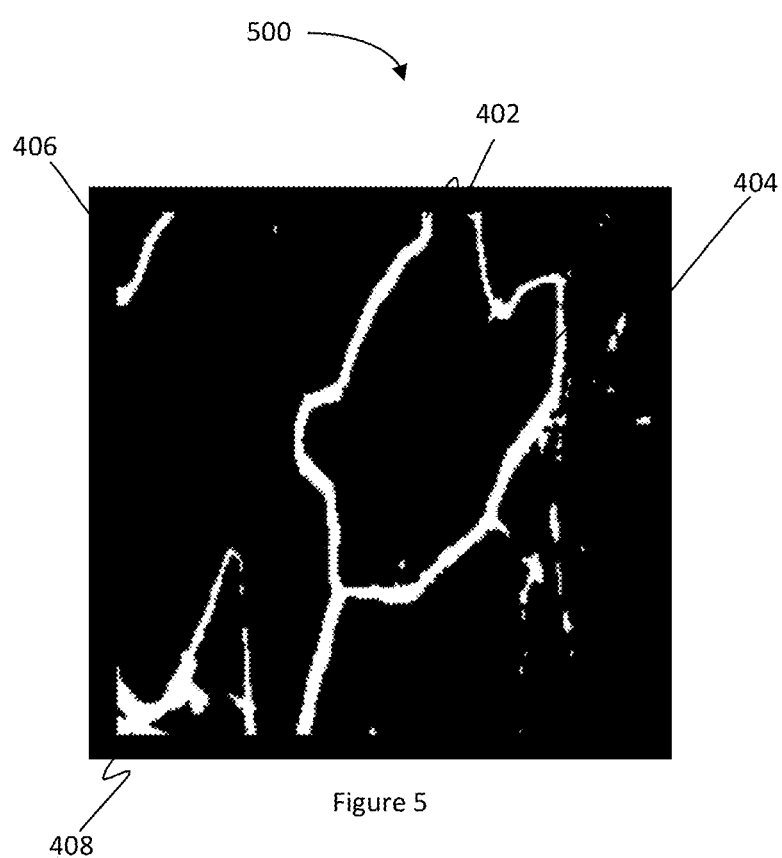
FIG. 5 is a masked image of the venuoles of FIG. 4.

Referring now to FIG. 4, there is shown an image 400 of venuoles. As can be seen in this image, there are several venuoles 402, 404, 406, 408 that can be easily discerned from other structures due to their darker hues. This is due to the fact that venuoles 402, 404, 406, 408 have a greater diameter and appear darker than arterioles Referring now to FIG. 5, there is shown a masked image 500 of the venuoles of FIG. 4. The image mask shown in this figure can be used to isolate the venuoles 402, 404, 406, 408 from the other structures in the image. Standard image masking functions are used to isolate the venuoles 402, 404, 406, 408 for analysis using the system that will provide superior results than a non-masked image. In one embodiment, the detection of venuoles 402, 404, 406, 408 comprises the steps of:

1) creating a binary matrix with the same dimensions as the original image;
2) determining for each pixel in the image, if the pixel is in the appropriate blood vessel color range and exceeds a darkness intensity threshold, a color intensity threshold or both a darkness and a color intensity threshold;
3) setting the corresponding bit in the matrix to true, otherwise set it to
false if the threshold of step 2) is true;
4) storing in a storage a position the pixel corresponding to the true bit position in the matrix as an identified venuole;
5) creating an image mask from the matrix and the stored pixel information to isolate the venuoles identified in steps 1)-4).

Figure 6:
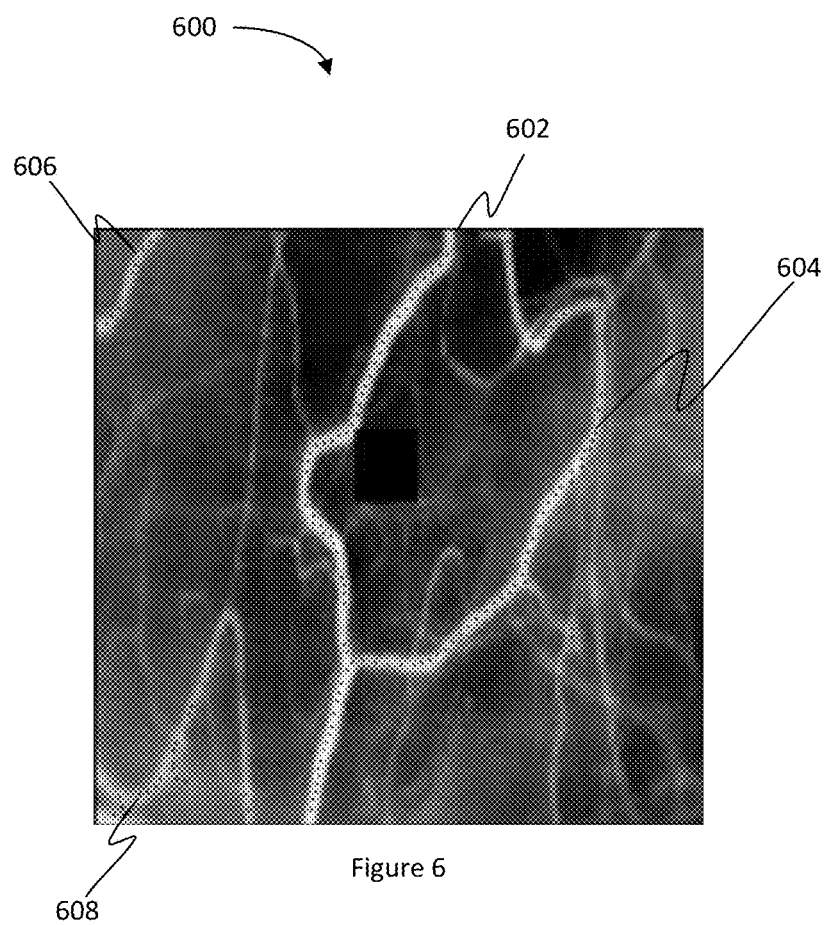
FIG. 6 is an image of venuole midpoints identified by dotted lines.

Referring now to FIG. 6, there is shown an image 600 of venuole midpoints identified by dotted lines. As can be seen, once the mask has been applied to the image in FIG. 4, the venuole midpoints 602, 604, 606, 608 can algorithmically be determined by the microprocessor in the device. In one embodiment, an arterial to venuole ratio is used to determine the venuole midpoints 602, 604, 606, 608. The arterial to venuole ratio is determined by counting the number of pixels in the image which are false in the venuole matrix, but match the appropriate blood vessel color range for an arterial and storing the result in a storage. Then, counting the number of true values in the venuole matrix and storing the results in a storage. The arterial to venuole ratio can then be calculated and the results for one or more than one images can be stored in the system or the device to perform the risk factor assessment for the patient.

Figure 7:
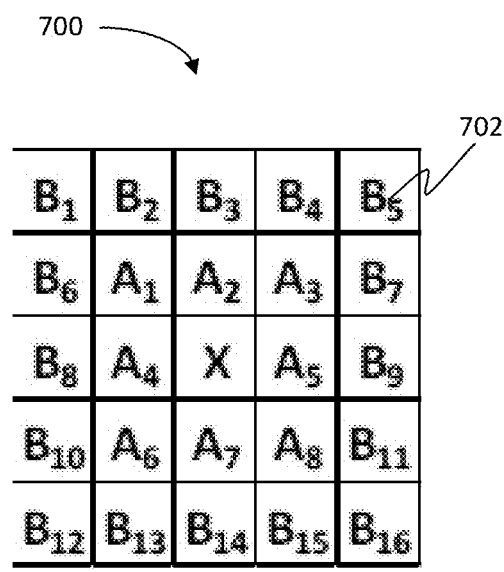
FIG. 7 is a matrix useful in identifying the venuole midpoints of FIG. 6.

Referring now to FIG. 7, there is shown a matrix 700 useful in identifying the venuole midpoints of FIG. 6. The system breaks the image into subsections for analysis. Then, the system uses a matrix, shown in FIG. 26, to identify a microangiopathy priority group 702 for each subsection. Each microangiopathy priority group 702 can then be analyzed or grouped together to determine a risk profile for the patient.

Figure 8:
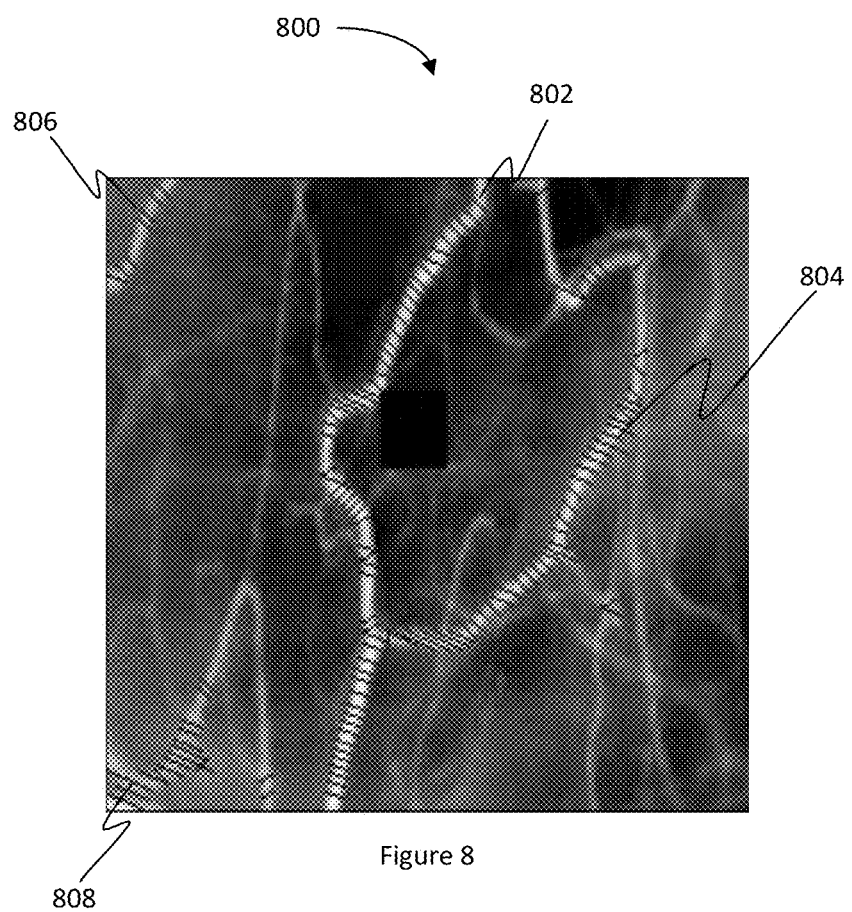
FIG. 8 is an image of venuole diameters and angles identified with slashes.

Referring now to FIG. 8, there is shown an image 800 of venuole diameters and angles identified with slashes 802, 804, 806, 808. Once again using the mask single image of FIG. 4, the system comprises non-transitory instructions executable on a microprocessor to perform an algorithmic analysis of venuole diameters and angles 802, 804, 806, 808. Then the venuole diameters and angles 802, 804, 806, 808 are identified by overlaying slashes for analysis of patient risk factors related to diabetes and pre-diabetes.

Figure 9:
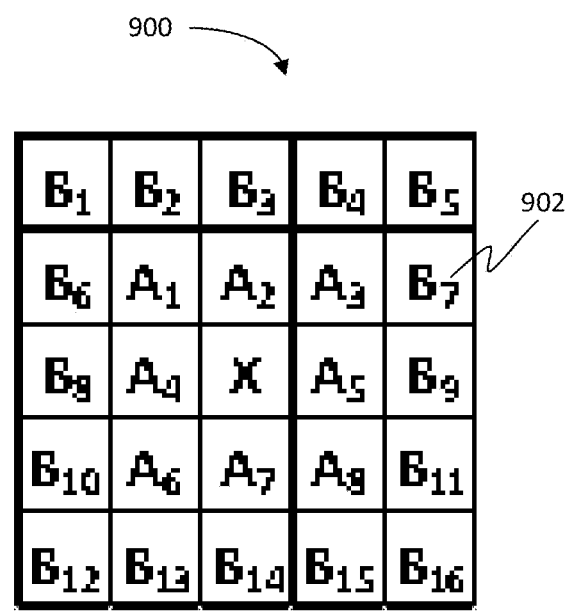
FIG. 9 is a matrix useful for identifying the venuole diameters and angles of FIG. 8.

Referring now to FIG. 9, there is shown a matrix 900 useful for identifying the venuole diameters and angles 802, 804, 806, 808 of FIG. 8. As can be seen, the system subdivides the image of the venuole diameters and angles 802, 804, 806, 808 into subsets. Then, microangiopathy priority groupings 902 are made for each subsection analyzed. Once each subsection has been analyzed and grouped, the system determines a risk factor for the patient based on one or more of the priority groupings 902 either alone or in combination.

Figure 10:
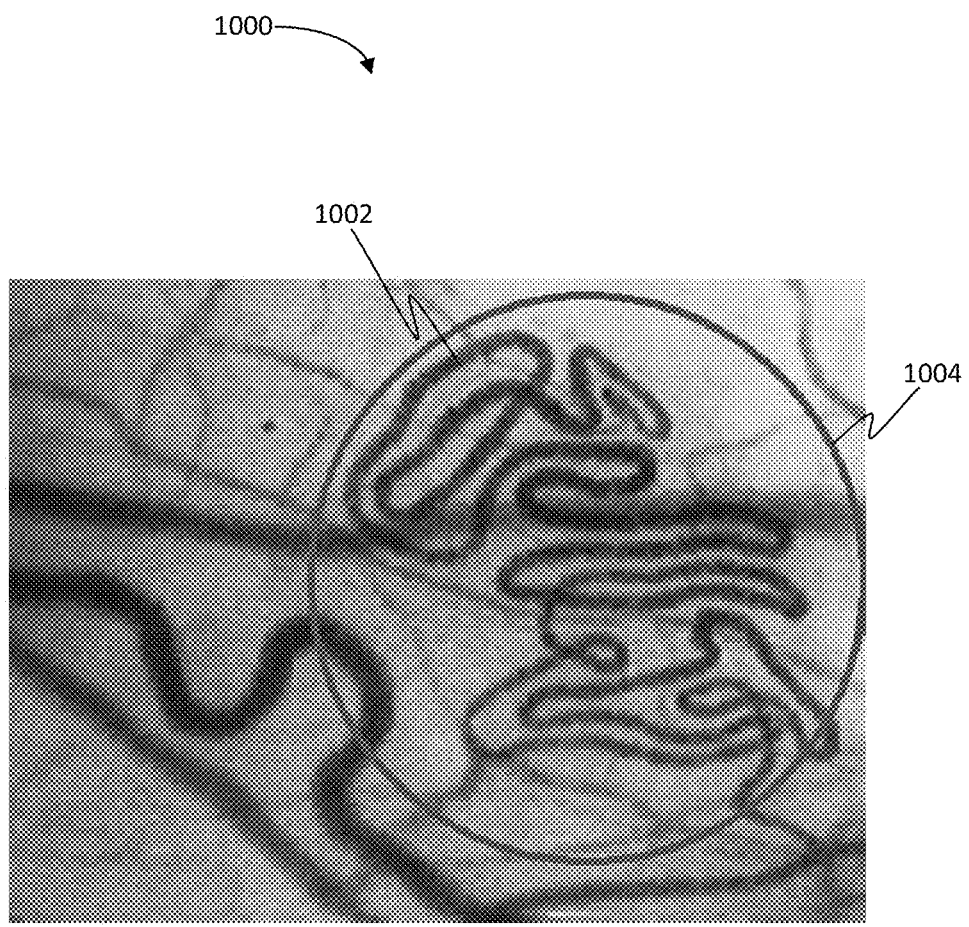
FIG. 10 is a first image of tortuous blood vessels.

Referring now to FIG. 10, there is shown a first image 1000 of tortuous blood vessels. As can be seen, tortuous blood vessels 1002 are highly erratic and easily identifiable in the image. However, to particularly point out the tortuous blood vessels a circle 1004 has been drawn around the area of interest.

Figure 11:
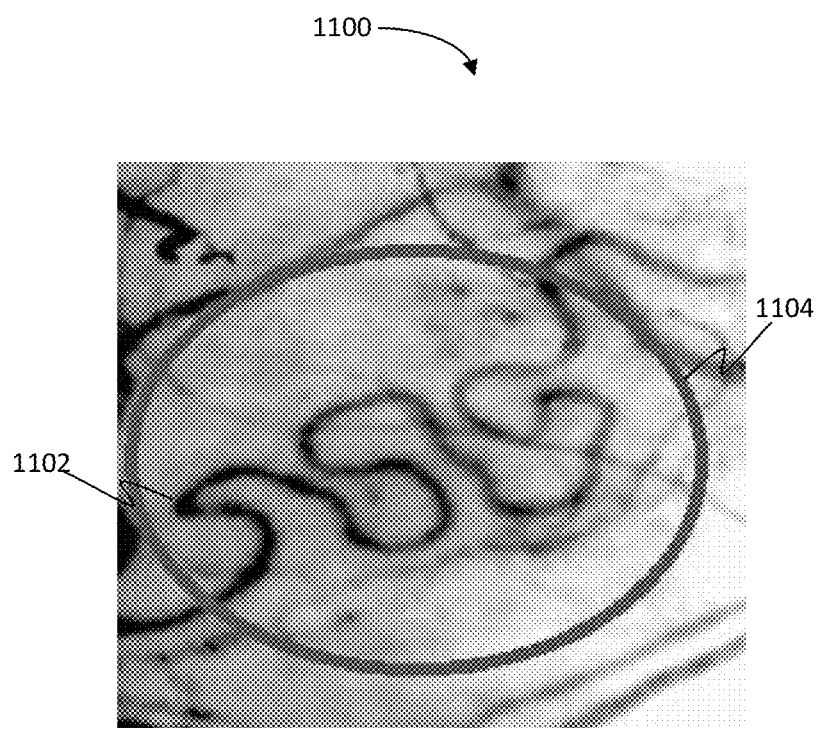
FIG. 11 is a second image of tortuous blood vessels.

Referring now to FIG. 11, there is shown a second image 1100 of tortuous blood vessels. This is another example of a tortuous blood vessel 1102 identified in a single image by the system. Again, a circle 1104 has been drawn around the area of interest. In both this image and in the previous image a mask is provided so that the tortuous blood vessels 1002 and 1102 stand out from the surrounding structures to make analysis faster and more accurate.

Figure 12:
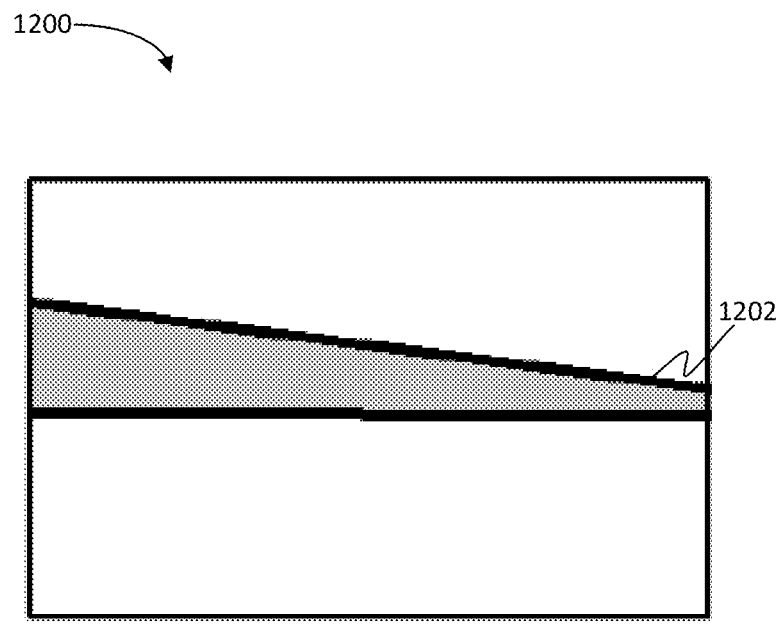
FIG. 12 is a first diagram of uneven blood vessels thickness.

Referring now to FIG. 12, there is shown a first diagram 1200 of uneven blood vessels thickness. As can be seen, blood vessels similar to this FIG. 1202 can be easily identified due to the variations in thickness. The system analyzes the single image for this risk factor.

Figure 13:
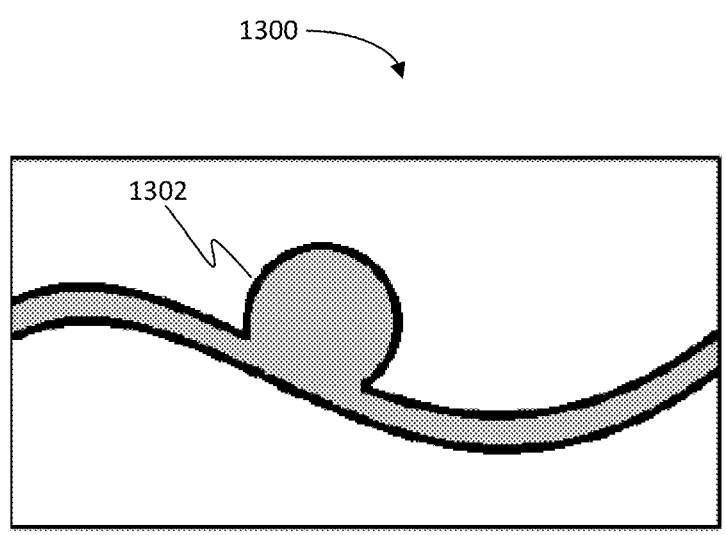
FIG. 13 is a second diagram of uneven blood vessel thickness.

Referring now to FIG. 13, there is shown a second diagram 1300 of uneven blood vessel thickness. In this example, the uneven blood vessel thickness shows as a bulge 1302 in the blood vessel wall. As can be appreciated by those with skill in the art with reference to this disclosure, the structure is also easily identifiable from the surrounding structures provided a proper mask is developed and overlaid to hide the surrounding structures that aren't of any interest in the analysis.

Figure 14:
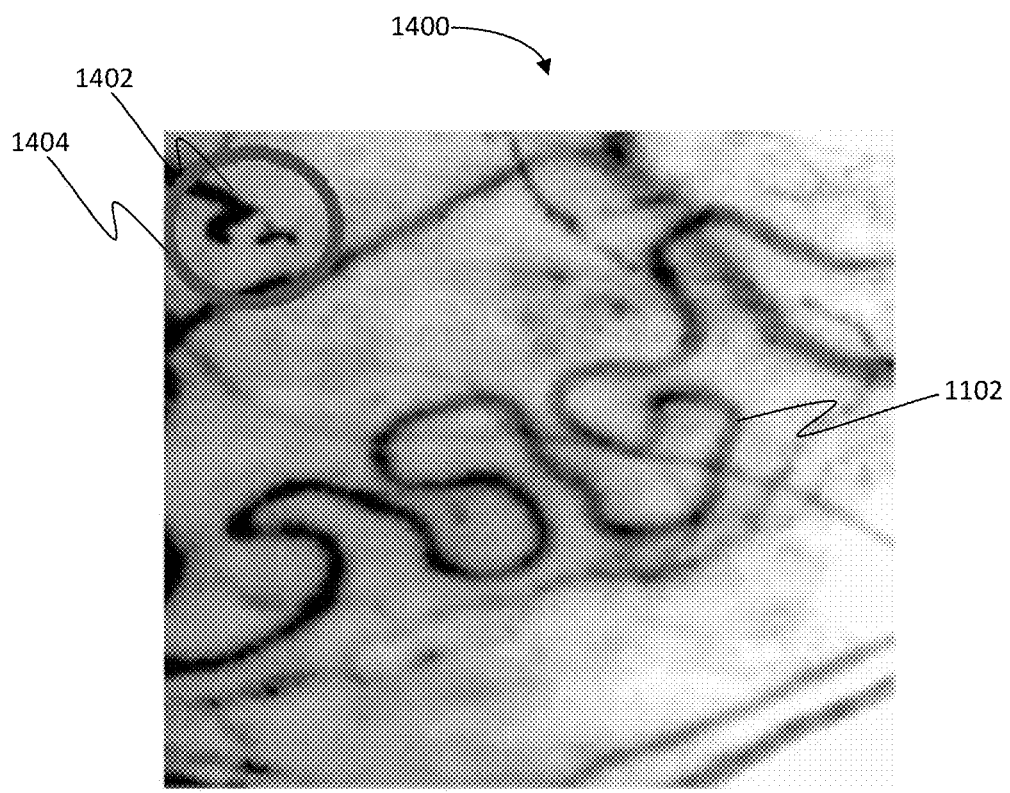
FIG. 14 is an image of a damaged blood vessel.

Referring now to FIG. 14, there is shown an image 1402 of a damaged blood vessel. As can be seen, this image contains both a tortuous blood vessel 1102 and a damaged blood vessel 1402. The damaged blood vessel 1402 is identified by a circle 1404 surrounding the area. Although more difficult to discern, damaged blood vessels 1402 similar to this can be easily isolated and analyzed using the algorithms executed by a microprocessor of the device.

Figure 15:
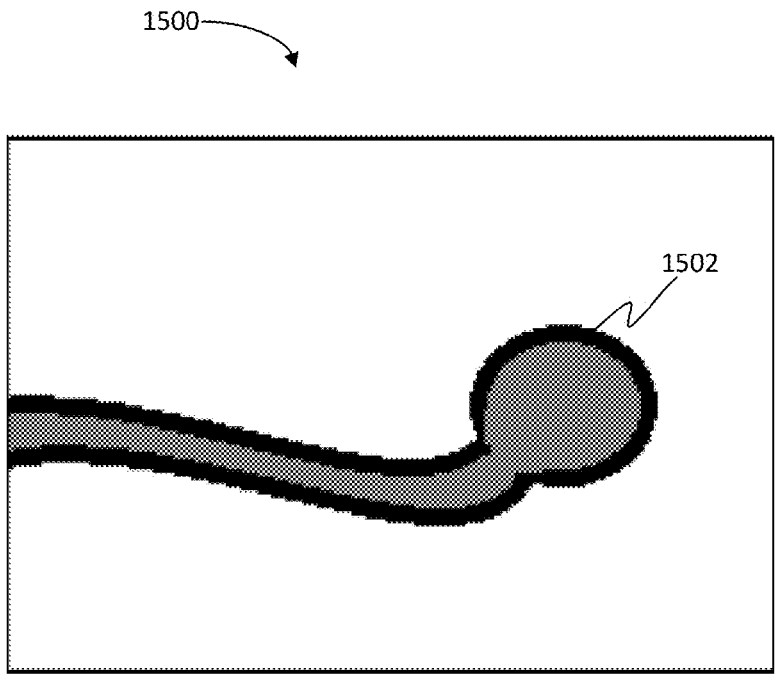
FIG. 15 is a diagram of a microaneurysm.

Referring now to FIG. 15, there is shown a diagram 1500 of a microaneurysm. As can be seen the microaneurysm 1502 would appear in the image as a bulbous ending to a venuole. The algorithms provided in the system will identify this risk factor from the surrounding structures.

Figure 16:
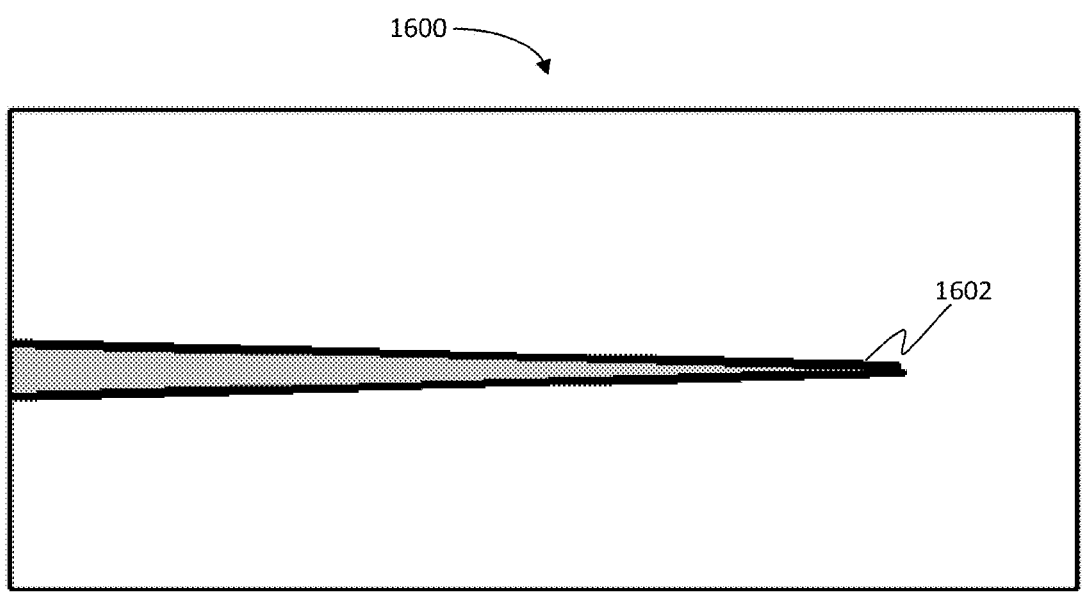
FIG. 16 is a diagram of a distended blood vessel.

Referring now to FIG. 16, there is shown a diagram 1600 of a distended blood vessel. The distended blood vessel 1602 shown in this diagram is similar to the uneven blood vessel of FIG. 12. Although similar, the system provides four separate identifications between the uneven blood vessel 1602 and the distended blood vessel so that the risk factors can be more accurately identified.

Figure 17:
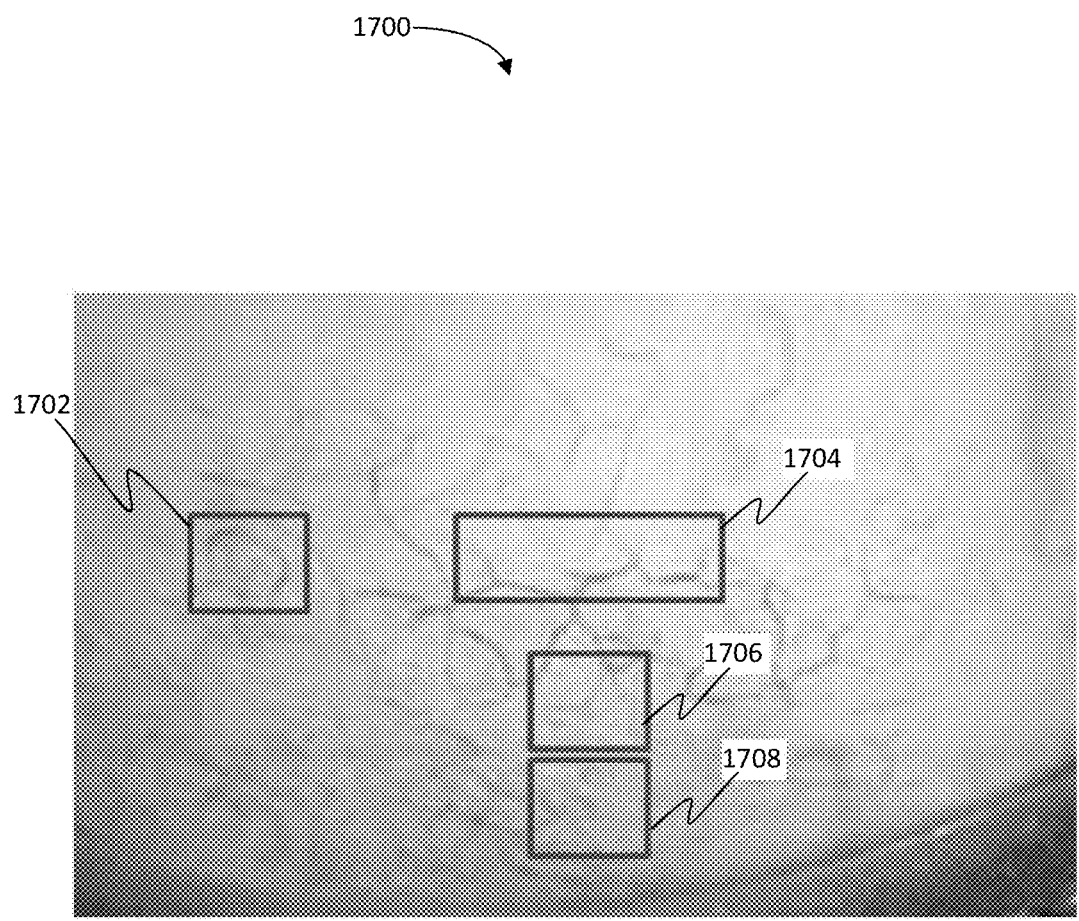
FIG. 17 is an image of sickle blood vessels.

Referring now to FIG. 17, there is shown an image 1700 of sickle blood vessels. As can be seen, there are several areas outlined that show sickle shaped blood vessels 1702, 1704, 1706 and 1708 that can be identified using the system in the device.

Figure 18:
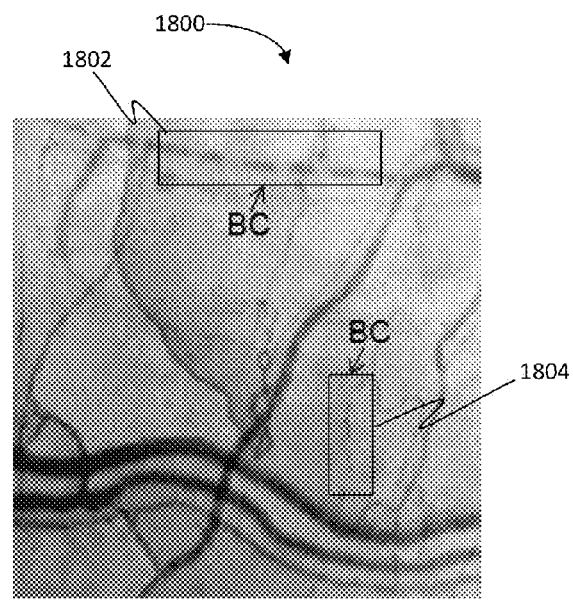
FIG. 18 is an image identifying boxcar flow in blood vessels.

Referring now to FIG. 18, there is shown an image 1800 identifying boxcar flow in blood vessels. In this image, there are two identified and outlined areas of boxcar flow 1802 and 1804 in blood vessels. Boxcar flow 1802 and 1804 appears on the images as a dashed line and they can also be easily identified by the system.

Figure 19:
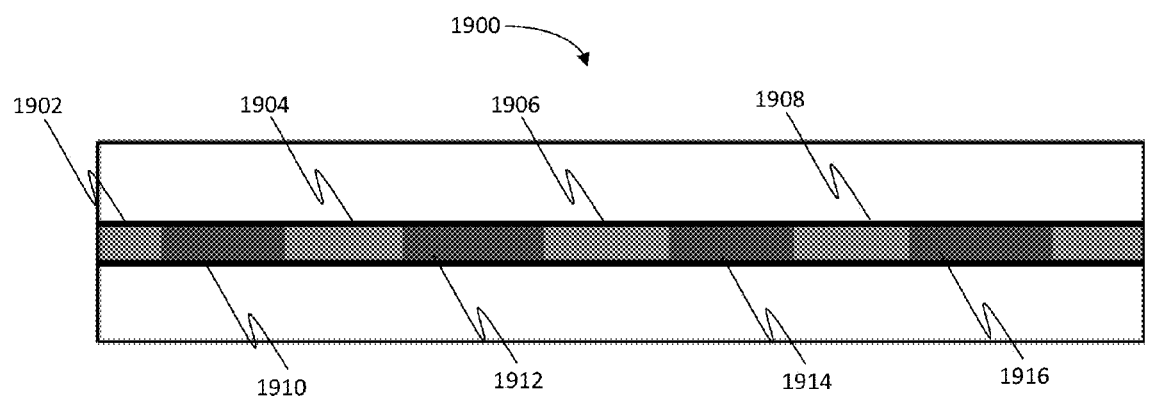
FIG. 19 is a diagram illustrating the boxcar flow of FIG. 18.

Referring now to FIG. 19, there is shown a diagram 1900 illustrating the boxcar flow of FIG. 18. Using the repeated light 1902, 1904, 1906 and 1908 and dark 1910, 1912, 1914 and 1916 areas, as shown here, the system can determine whether or not boxcar flow is present in the image during analysis.

Figure 20:
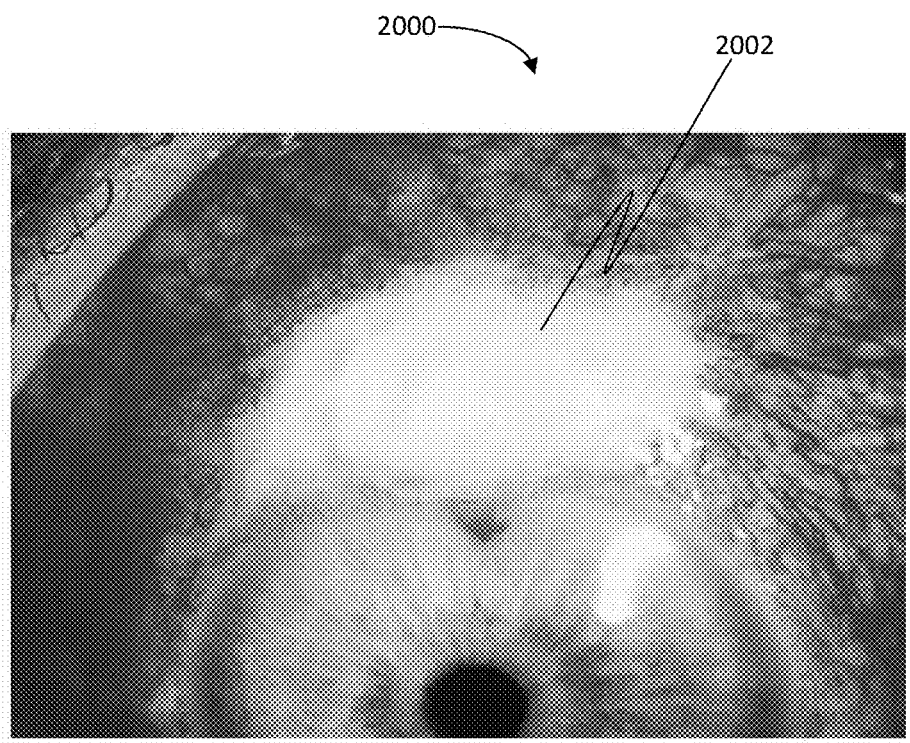
FIG. 20 is an image showing ischemic sites.

Referring now to FIG. 20, there is shown an image 2000 showing ischemic sites. As can be seen, the ischemic site 2002 shown in this image appears white due to a restriction in blood flow to that particular area of the eye. As can be appreciated, insufficient blood supply causes tissue to become starved of oxygen and can lead to serious tissue damage if left untreated over long periods of time.

Figure 21:
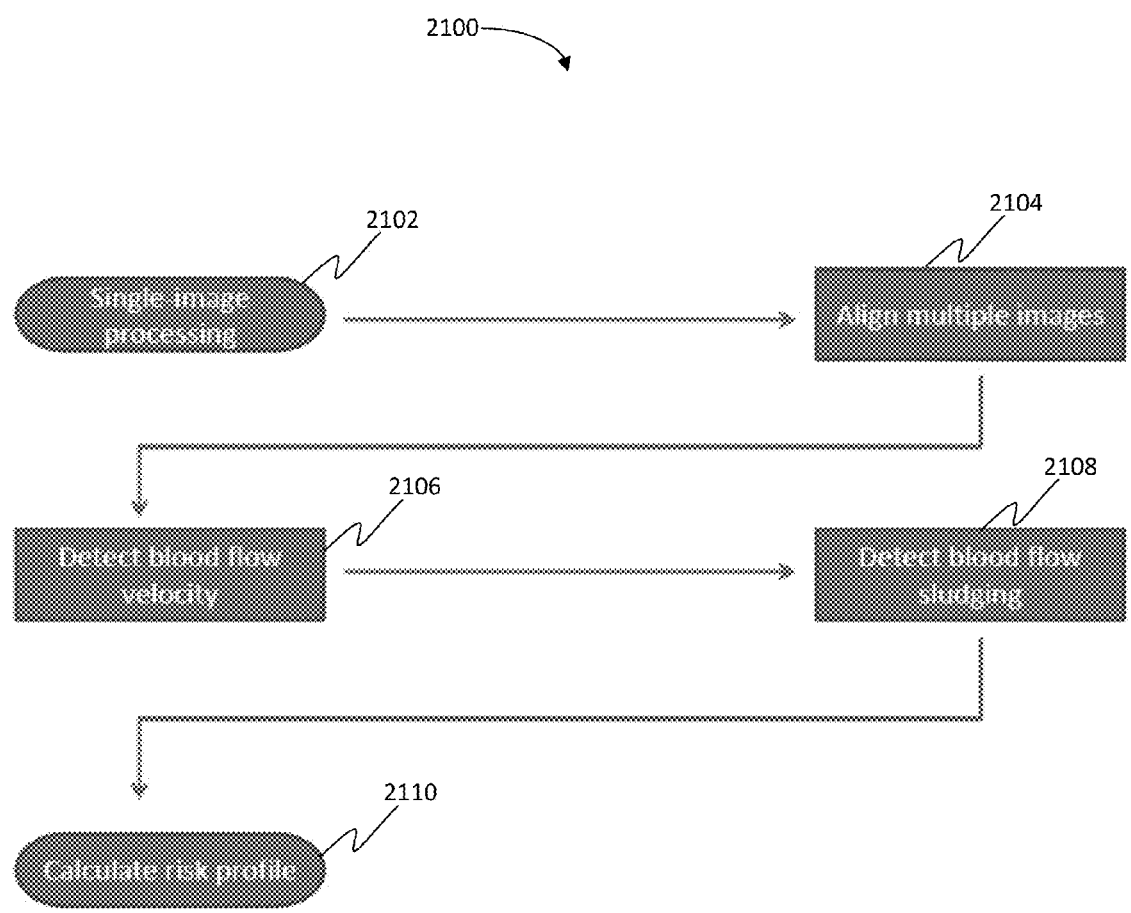
FIG. 21 is a series of pixels from multiple images to be registered and aligned, according to one embodiment.

Referring now to FIG. 21, there is shown a series of pixels 2100 from multiple images to be registered and aligned, according to one embodiment. After the system has analyzed a single image 2102, or multiple single images, to determine a patient's risk factor for diabetes or pre-diabetes, all the images taken by the device are first aligned 2104, then analyzed. In order to ensure accuracy for detecting blood flow velocity 2106 and blood flow sludging 2108, multiple images are needed to identify the movement of blood through the venuoles. As can be appreciated, a single image is insufficient for determining the velocity of blood flowing 2106 through the eye of the patient. After the blood flow velocity 2106 is determined by the system, an analysis is performed to detect blood flow sludging 2108. Blood flow sludging 2108 occurs when red blood cells become massed along the walls of the blood vessels and reduce the lumen of the vessels and the rate of blood flow. Based on the detected blood flow velocity 2106 and the detected blood flow sludging 2108, the system then calculates the risk profile 2110.

Figure 22:
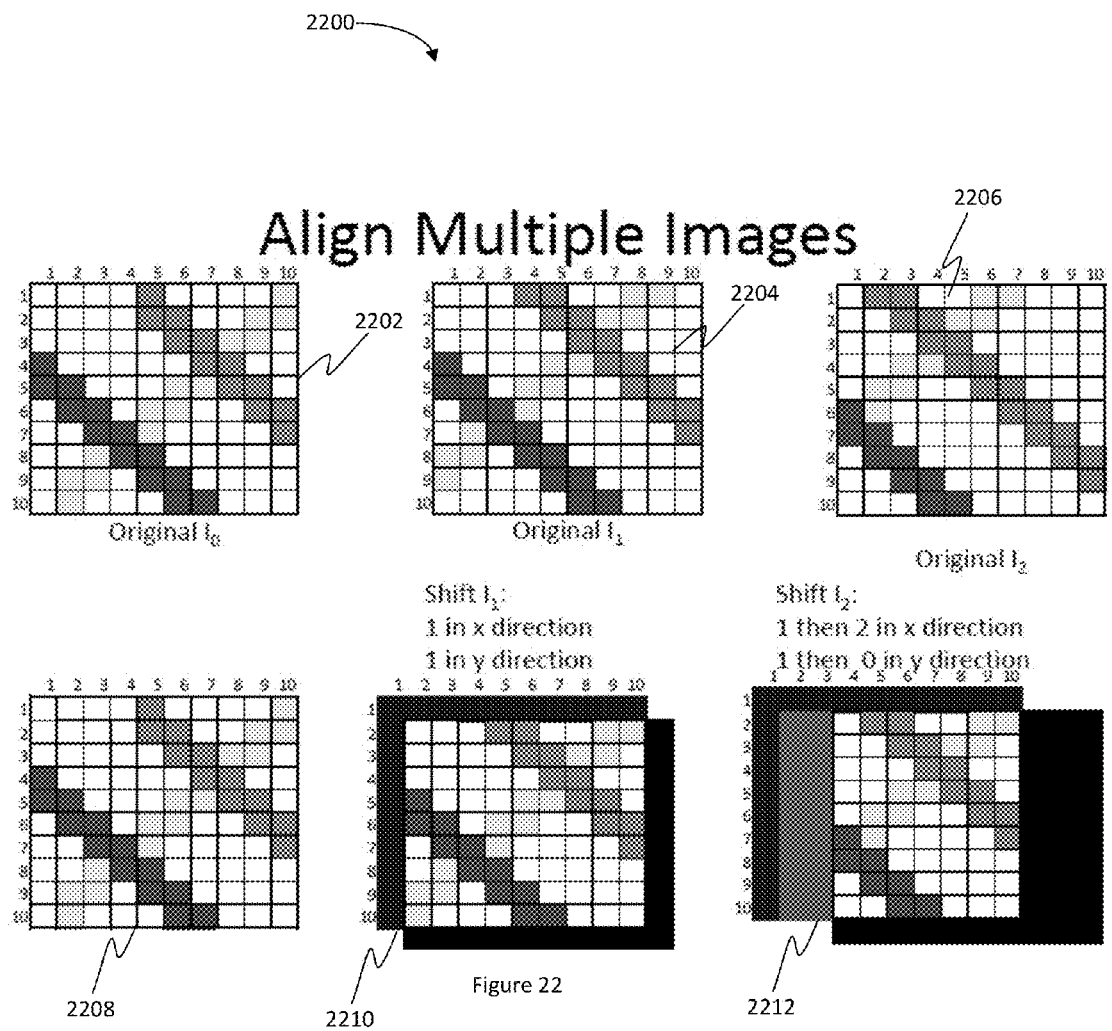
FIG. 22 is a series of images useful for aligning the multiple images of FIG. 21.

Referring now to FIG. 22, there is shown a series of images 2200 useful for aligning the multiple images of FIG. 21. As can be seen in this series of six images 2202, 2204, 2206, 2208, 2210 and 2212, in order to analyze blood flow and blood flow sludging, the series of images must be aligned, or registered, with one another. Image alignment and registration involves translation and rotation of the images 2202, 2204, 2206, 2208, 2210 and 2212 so that the resultant image is an overlay of common areas of the images 2202, 2204, 2206, 2208, 2210 and 2212. Each of the images 2202, 2204, 2206, 2208, 2210 and 2212 is analyzed for commonalities and then a determination is made on how to translate and/or rotate each of the images. It is common practice to select one image as a master image, or reference image 2202, so that each of the other images 2204, 2206, 2208, 2210 and 2212 will be aligned, or registered, with this image. In this example, original image 2202 is used as the master or reference image.

Figure 23:
FIG. 23 is a matrix useful for aligning the images of FIG. 22.

Referring now to FIG. 23, there is shown a matrix 2300 useful for aligning the images of FIG. 22. As can be seen, each image is analyzed for alignment and registration and displayed in this matrix. The amount and location that each image needs to be shifted, and the direction of the shift is identified in the matrix 2302. Then, the system transforms each of the images by moving all the pixels in the image in the amount and direction specified in the matrix 2300. Once this operation is complete then all of the images are overlaid upon each other and all the transforms of pixels are summed with each other in order to produce the final image.

Figure 24:
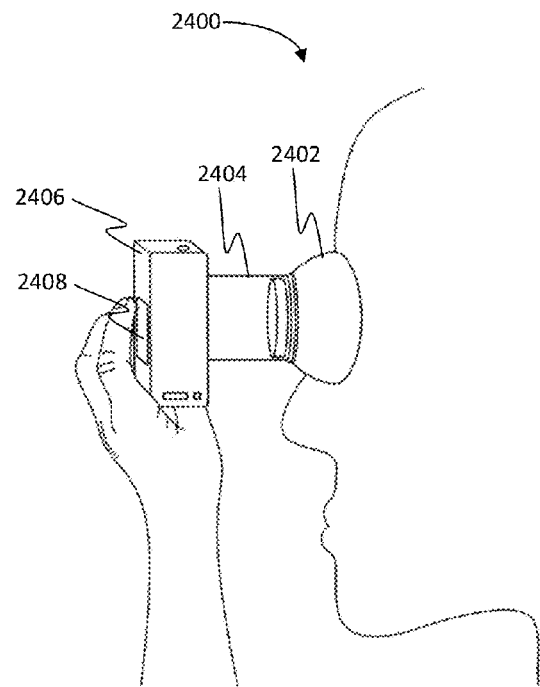
FIG. 24 is a diagram of a device for automatic noninvasive screening for diabetes and pre-diabetes.

Referring now to FIG. 24, there is shown a diagram 2400 of a device for automatic noninvasive screening for diabetes and pre-diabetes. As can be seen, the device comprises an eyepiece 2402 that is connected to a tube 2404 having a proximal and distal end, where the eyepiece 2402 is attached to the distal end. The tube 2404 also comprises an exterior and interior portion. Lighting 2502 is affixed to the interior portion of the tube 2404. Additionally a magnifying lens 2504 is also affixed to the interior portion near the proximal end of the tube 2404. The proximal end of the tube 2404 is affixed to a camera body 2406, where the camera body 2406 has an interior and exterior portion. In one embodiment, a touch-screen 2408 is affixed to the camera body 2406 opposite to the tube 2404. The interior portion of camera body 2406 comprises at least a camera sensor, a microprocessor and a storage for storing images. The camera sensor can be either a CMOS, CCD or any other type of imaging sensor as will be understood by those with skill in the art with reference to this disclosure. The device can further comprise a hardware communications port, a wireless transmitter, or both a hardware communications port and a wireless transmitter for downloading the images from the storage in the device to an external storage or archival repository. Additionally, the device can comprise a wired trigger, a wireless trigger, or both a wired and wireless trigger for activating the device to take an image of a patient's eye to analyze the risk factors for diabetes or pre-diabetes.

In one embodiment, the device can comprise a handheld computer with a touch-screen 2408, a camera, a lens for magnification, a light source, such as, for example an LED, communications means, such as, for example, WiFi or Bluetooth, and a plastic shield that is placed against the forehead of the patient.

In another embodiment, the device can be similar to a combination of a smartphone, with an augmented camera lens, and an optometrists' slit lamp.

The device can comprise non-transitory instructions executable on a processor to perform image processing algorithms. The image processing algorithms can examine one or more than one image to detect the presence, and measure when appropriate, abnormalities in the microcirculation of the patient. The results of analysis of the images processed can be correlated to the HbA1c values currently known and updated from acquired clinical studies and ongoing research to improve the accuracy of the algorithms and results.

In another embodiment, the device can transmit image data to one or more other computers, or to a centralized location for processing. The cost of the device can be reduced by distributing the actual processing and analysis of the one or more than one image to one or more than one computers that have greater processing power. This can speed the results of the analysis and the risk profile can then be transmitted back to the device in either a wired or wireless manner during a patient consult.

In another embodiment, the device can be a stand-alone device that comprises embedded software and hardware to perform the analysis. Additionally, the device can comprise a graphical user interface (GUI) to ease operation of the device.

In one embodiment, the algorithms to analyze the one or more than one images for a large set of abnormalities, for improved accuracy. Results can be obtained using any single abnormality, but accuracy is increased by performing multiple analysis on the one or more than one image. Prior research correlates abnormalities with retinopathy. New research correlates abnormalities with HbA1c. In one embodiment, the set of abnormalities can be assigned three levels of importance.

The set of abnormalities and the groups comprise:
Group A (highest importance)
  abnormal vessel diameter
  vessel tortuosity
  uneven vessel thickness
  damaged vessel
  microaneurysm
Group B
  abnormal vessel distribution
  blood flow sludging
  ischemic sites
  abnormal Arteriole: Venule ratio
  hemosiderin deposits
  abnormal blood flow velocity
Group C
  abnormal morphology
  distended vessel
  "boxcar" blood flow phenomena (trickled flow)
  comma sign As will be understood by those with skill in the art, the list of abnormalities can change with new research and the list is not meant to be limiting.

Figure 25:
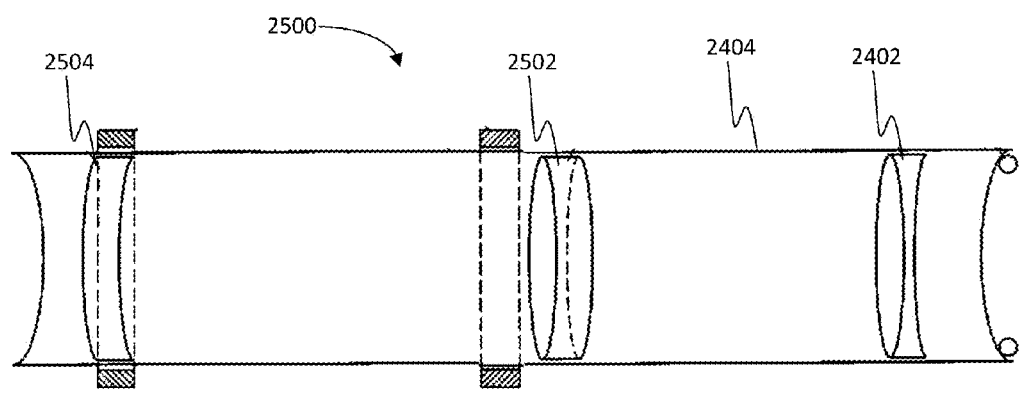
FIG. 25 is a cross-sectional diagram of a portion of the device of FIG. 24.

Referring now to FIG. 25, there is shown a cross-sectional diagram of a portion of the device of FIG. 24. As can be seen, the eyepiece 2402 connected to the distal end of the tube 2404 is positioned such that a target light is visible to the patient so that they can focus their eye on the target. In one embodiment, light emitting diodes are used to illuminate the patient's eye to improve photographic quality of the image obtained. The magnifying lens 2504 at the proximal end of the tube 2404 is of the correct focal length for the tube 2404 distance from the patient's eye to the imaging sensor. This insures a fixed focal length so that the images taken are always in focus.

Referring now to FIG. 26, there is shown a table 2600 prioritizing various microangiopathy with visible indicators. The table 2600 identifies a priority group, a microangiopathy, a scientific basis and an observational description of each of the risk factors identifiable from either a single image or multiple images. The group priority is directly related to the risk of diabetes or pre-diabetes. Clinical studies are currently underway to make sure that the correlation between the microangiopathy and the risk factors are correct. The observational descriptions are the basis of the algorithms used in the system to identify the risk factors from images taken by the device. As can be appreciated, the risk factors are prioritized from A, the most severe risk factor, to C the least severe risk factor. The risk factor analysis weighs all of the risk factors in accordance to their priority. For example, a patient with three A risk factors would be identified as either diabetic or pre-diabetic depending upon the patient history. Whereas, a patient with two C and one B risk factors would not be identified as either diabetic or pre-diabetic, again in relation to patient history and health.

Figure 27:
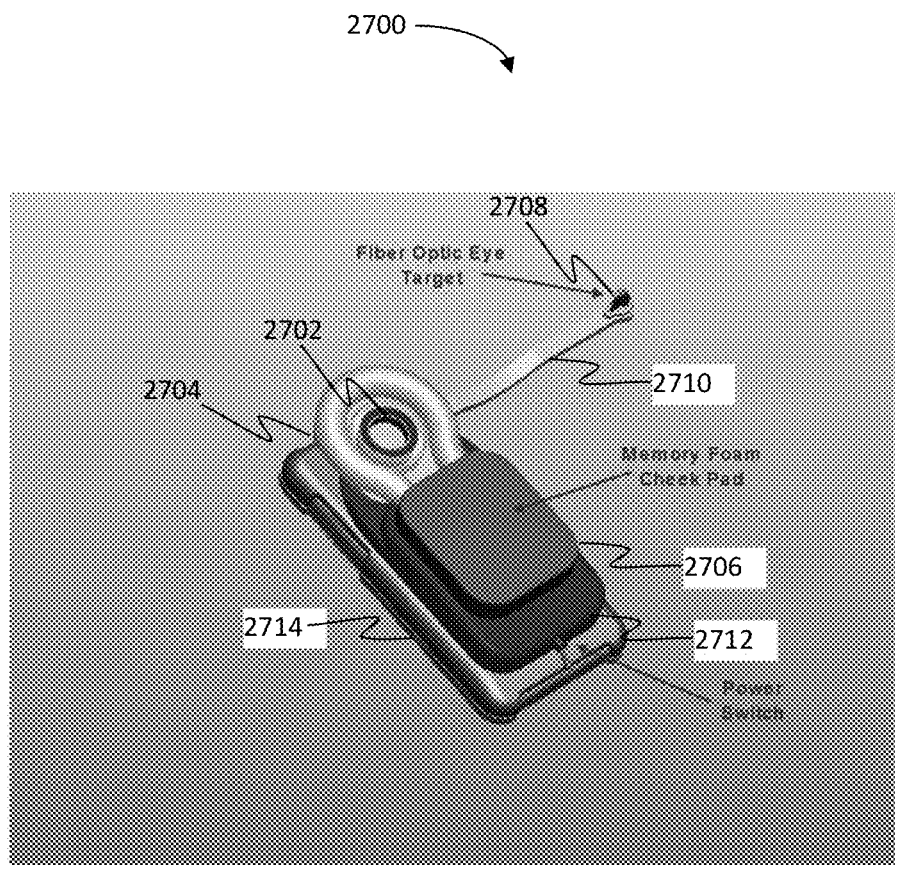
FIG. 27 is a diagram of an embodiment of the device.

Referring now to FIG. 27, there is shown a diagram 2700 of an embodiment of a device for automatic noninvasive screening for diabetes and pre-diabetes. As can be seen, the device comprises a lens 2702, which has a light source wrapped around it. The light source can be composed of a silicon tube 2704 with LED lights placed inside of the tube 2704. The LED's can be directed radially out, away from the lens 2702. The placement of the light source allows the silicon tube 2704 to direct light to the eye in a uniform, diffuse manner, as well as minimize reflected glare. When the device is in use, the light source 2704 is placed against the patient's face that serves to control the lighting by blocking out ambient light.

The device also comprises a foam pad 2706, which the patient also rests against their face. This provides a comfortable resting surface for the device. The foam pad 2706 can be made out of any type of foam; however, memory foam is preferable. The device can further comprise a fiber optic fixation light 2708. The purpose of the fixation light 2708 is to allow the patient to focus their eye on a specific location, which allows the device to capture an image of the conjunctiva. The fixation light 2708 is mounted on a post 2710 which can rotate 180° around the lens 2702. The fixation light 2708 is placed on the opposite side of the face from the eye being imaged. This placement causes the eye being imaged to look towards the middle of the face, exposing as much of the conjunctiva as possible for imaging. Once the imaging of one eye is completed, the fixation light 2708 can be rotated 180° to the opposite side of the device, and the device can then be placed on the other eye in order to image the other eye.

The device can also comprise a camera body 2712 and a handheld computer 2714. The light source 2704 is wrapped around the lens 2702, the lens 2702 is coupled to a camera body 2712, and the camera body 2712 is mounted to a handheld computer 2714.

Figure 28:
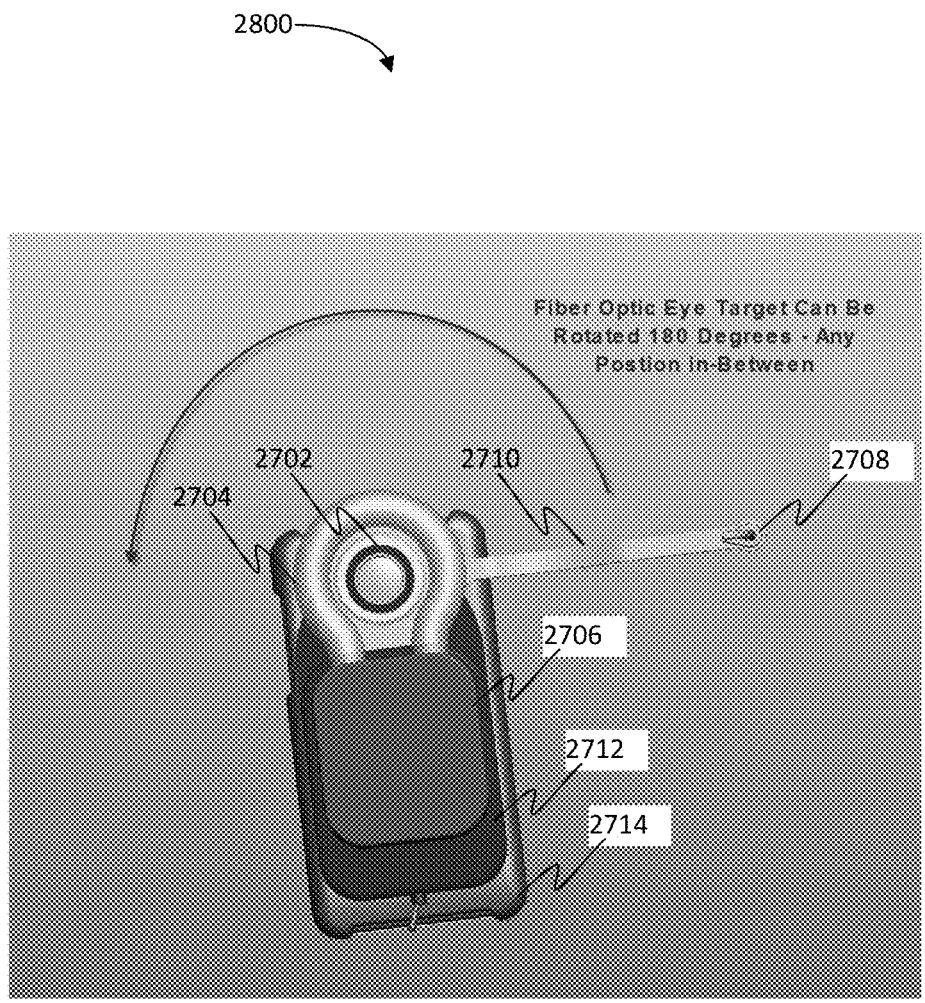
FIG. 28 is a diagram of an embodiment of the device, showing the 180 degree rotation of the fixation light 2708.

Referring now to FIG. 28, there is shown a diagram 28 of an embodiment of the device, wherein the 180° rotation of the fixation light 2708 is demonstrated. The fixation light 2708 can also be stopped at any point in between, if a different position of the eye is desired.

Figure 29:
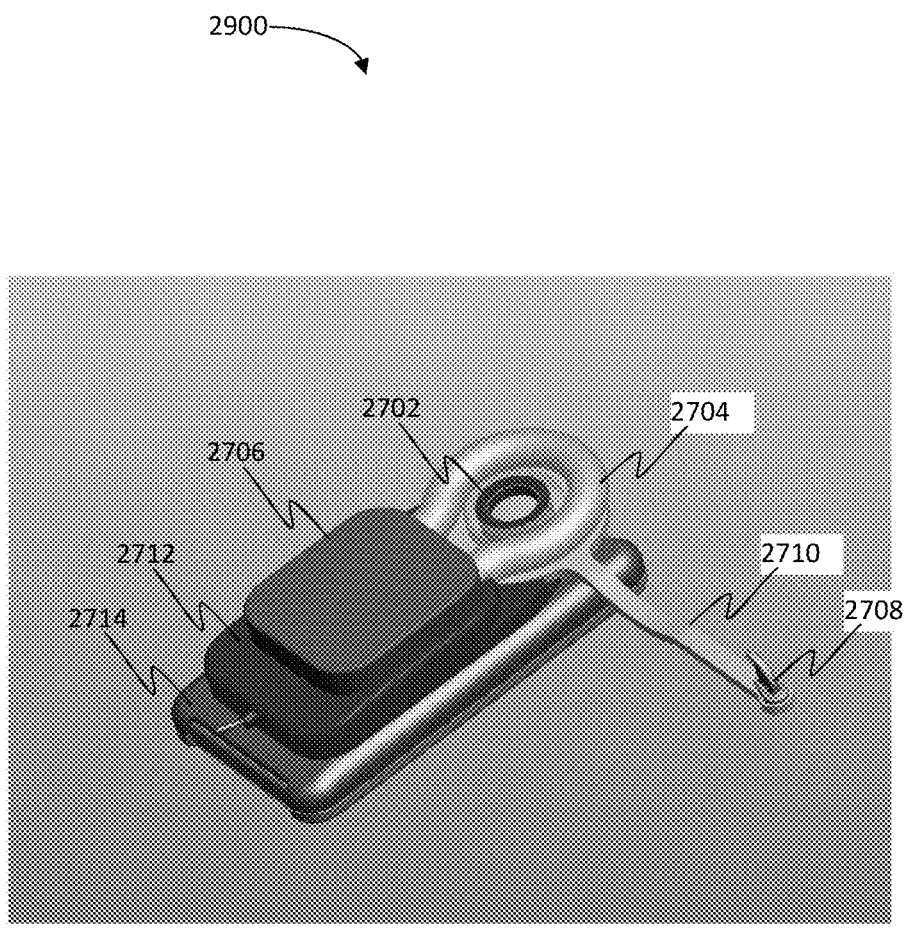
FIG. 29 is a diagram of an embodiment of the device viewed from the side.

Referring now to FIG. 29, there is shown a diagram 2900 of an embodiment of the device, wherein the device is viewed from the right side. As can be seen, the light source 2704 can comprise a tube 2404 wrapped around the lens 2702. The lens 2702 can be coupled to the camera body 2712, and the camera body 2712 can be coupled to the handheld computer 2714. Also coupled to the lens 2702 is the fixation light 2708, which rotates 180° around the lens 2702.

Figure 30:
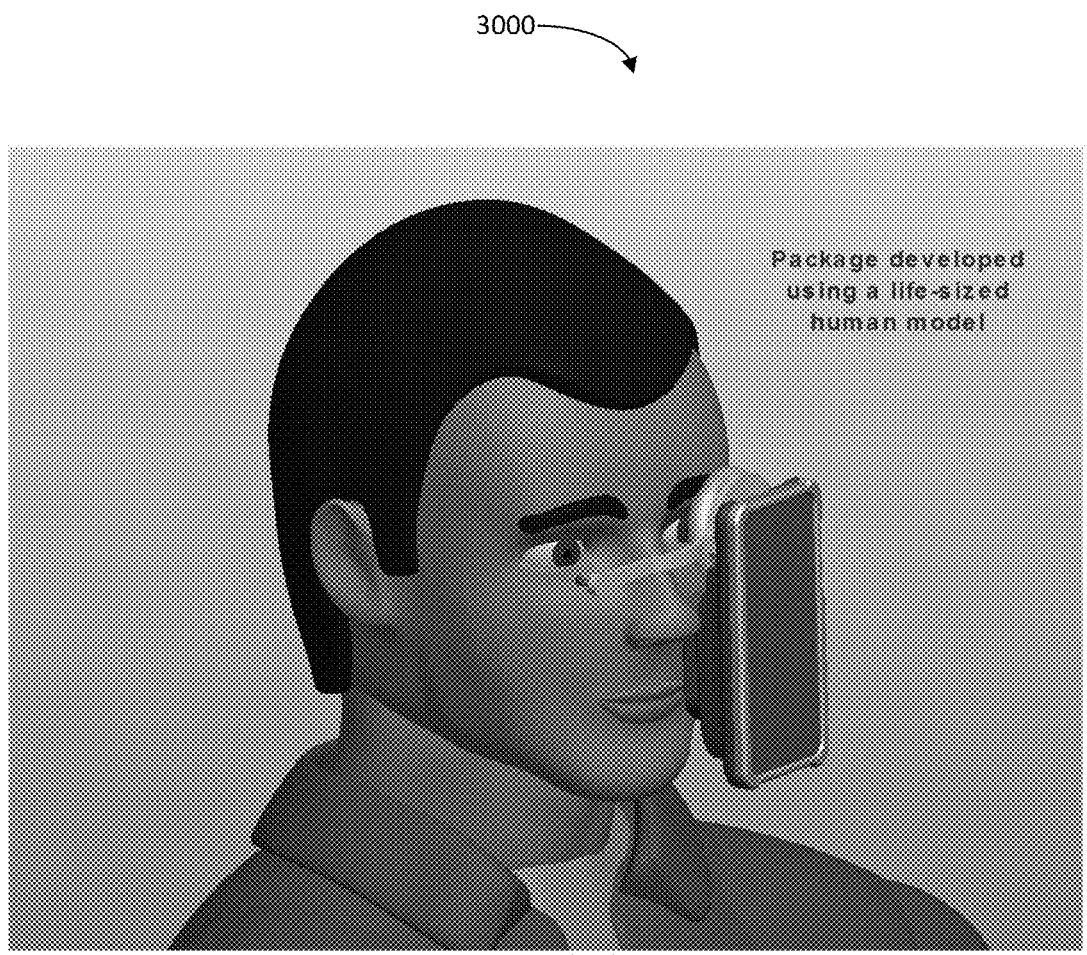
FIG. 30 is a diagram of an embodiment of the device being used on a life-sized human model.

Referring now to FIG. 30, there is shown a diagram 3000 of an embodiment of the device, wherein the device is being used on a life-sized human model. As can be seen, both the light source 2704 and the foam pad 2706 rest against the patient's face. The fixation light 2708 is located opposite the eye being imaged, and can be rotated 180° around the lens 2702 to the desired position.

Figure 31:
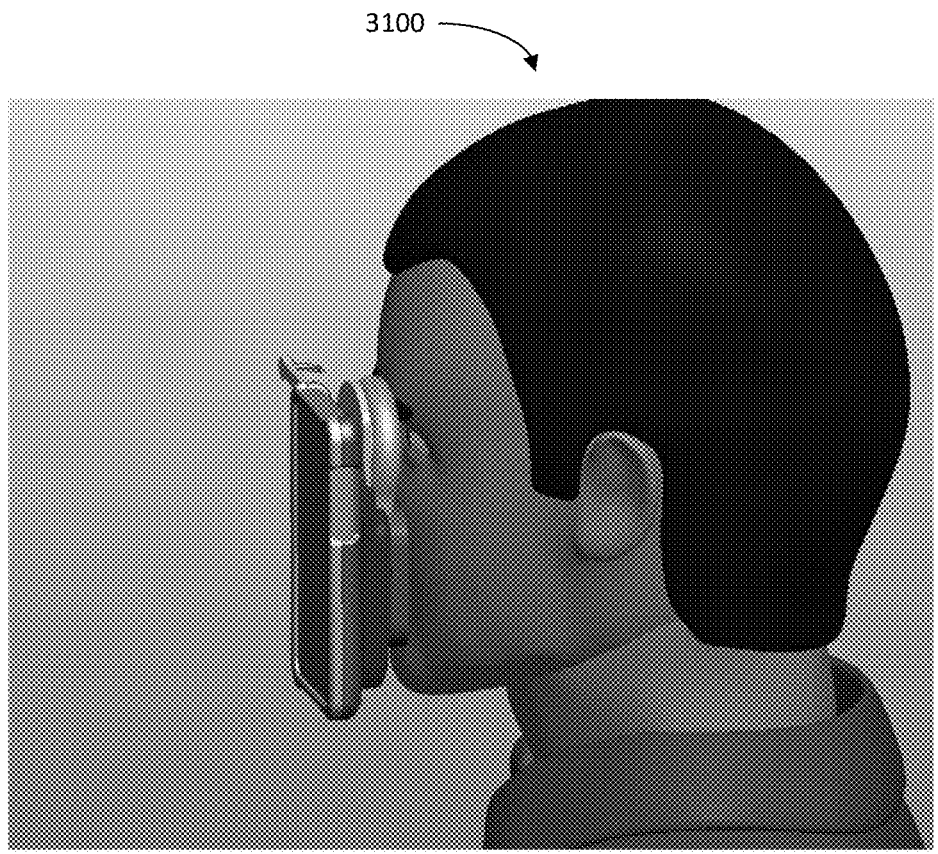
FIG. 31 is a diagram of an embodiment of the device being used on a life-sized human model as viewed from the side.

Referring now to FIG. 31, there is shown a diagram 3100 of an embodiment of the device, wherein the device is being used on a life-sized human model, and the device is being viewed from the side. As can be seen, both the light source 2704 and the foam pad 2706 rest against the patient's face. The fixation light 2708 is located opposite the eye being imaged, and can be rotated 180° around the lens 2702 to the desired position.

Figure 32:
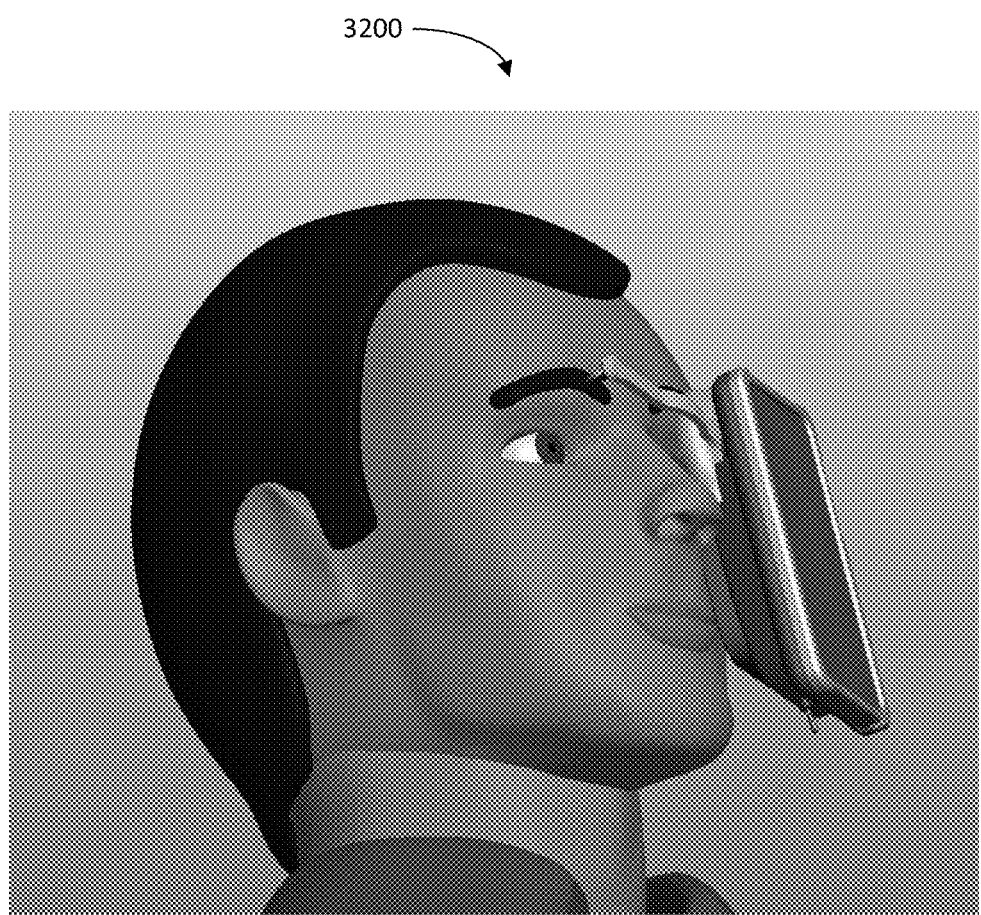
FIG. 32 is a diagram of an embodiment of the device being used on a life-sized human model as viewed from below.

Referring now to FIG. 32, there is shown a diagram 3200 of an embodiment of the device, wherein the device is being used on a life-sized human model, and the device is being viewed from below and to the left. As can be seen, both the light source 2704 and the foam pad 2706 rest against the patient's face. The fixation light 2708 is located opposite the eye being imaged, and can be rotated 180° around the lens 2702 to the desired position.

Figure 33:
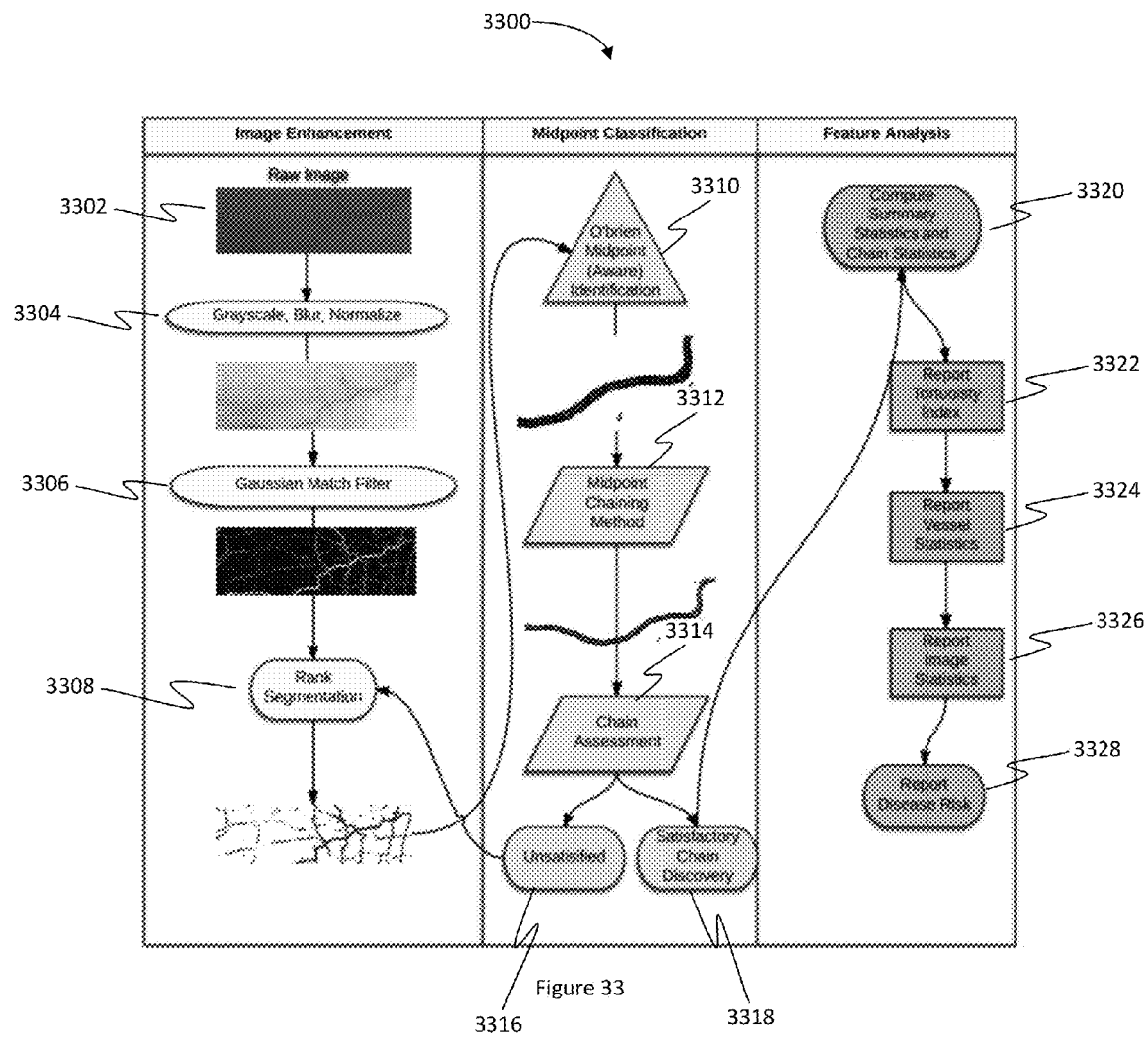
FIG. 33 is a diagram of some steps of a method for image processing useful for the device of FIG. 24.
Figure 34:
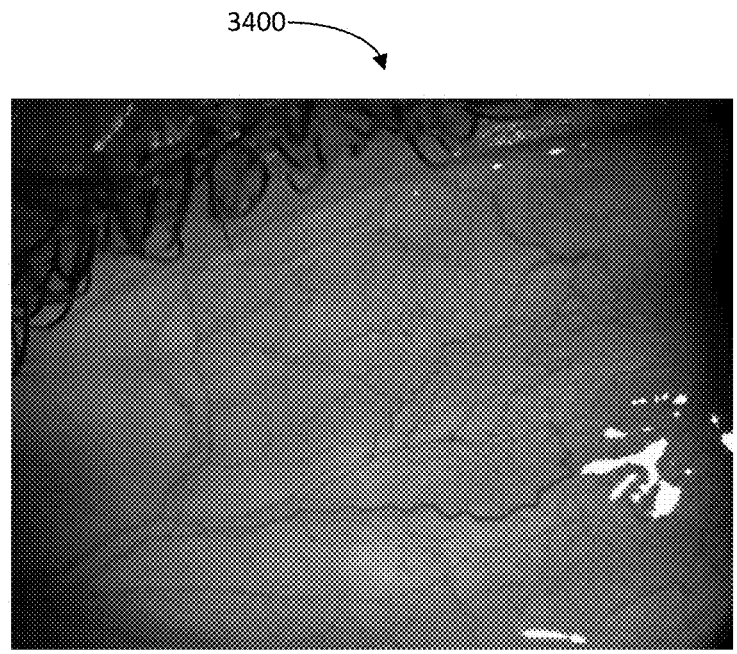
FIG. 34 is a color image of a patient's eye prior to processing.
Figure 35:
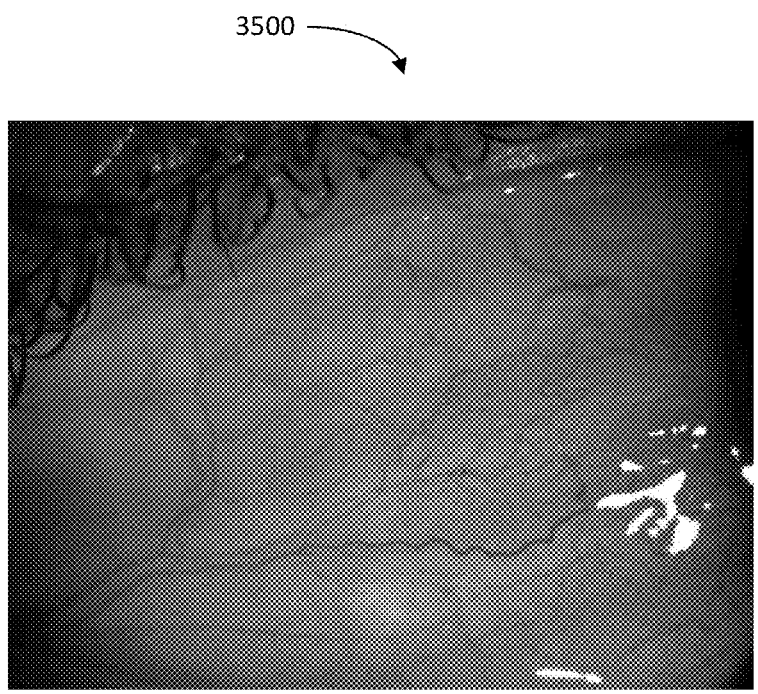
FIG. 35 is a grayscale image of a patient's eye.
Figure 36:
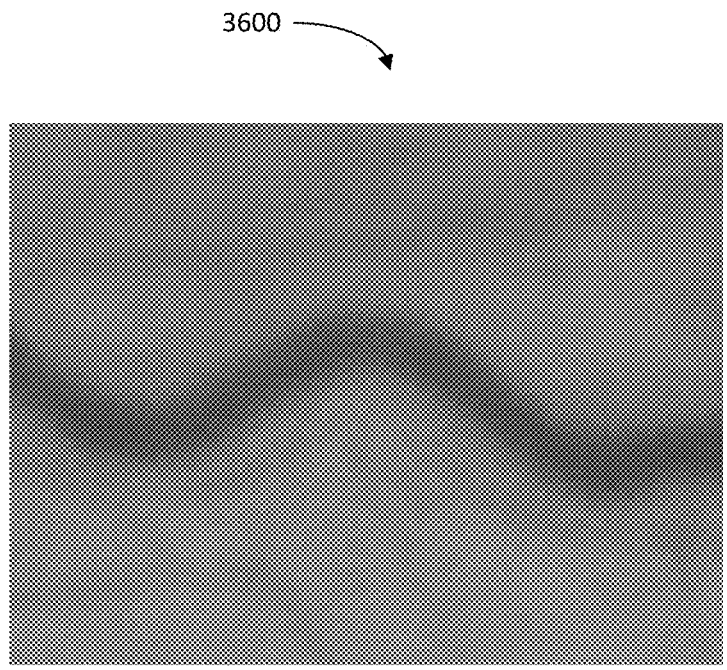
FIG. 36 is a close-up of the grayscale image of FIG. 35.
Figure 37:
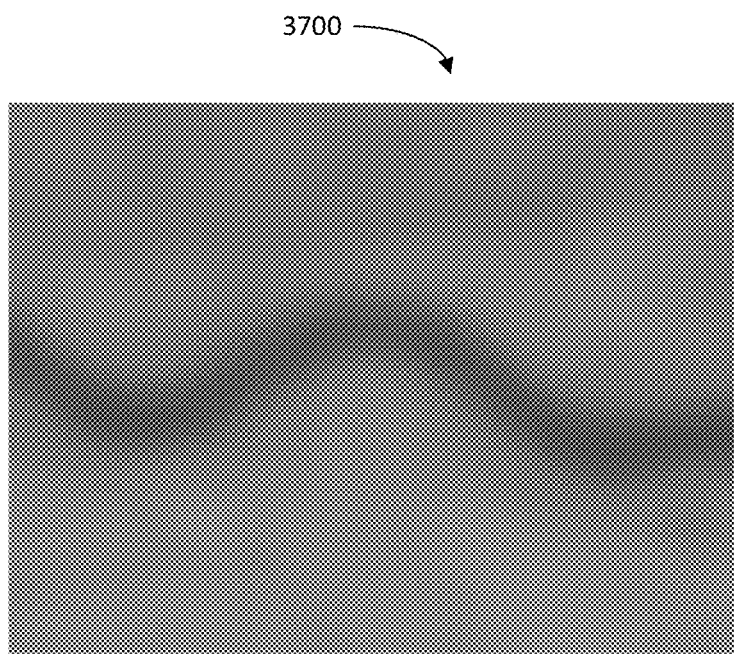
FIG. 37 is the grayscale image after blurring.
Figure 38:
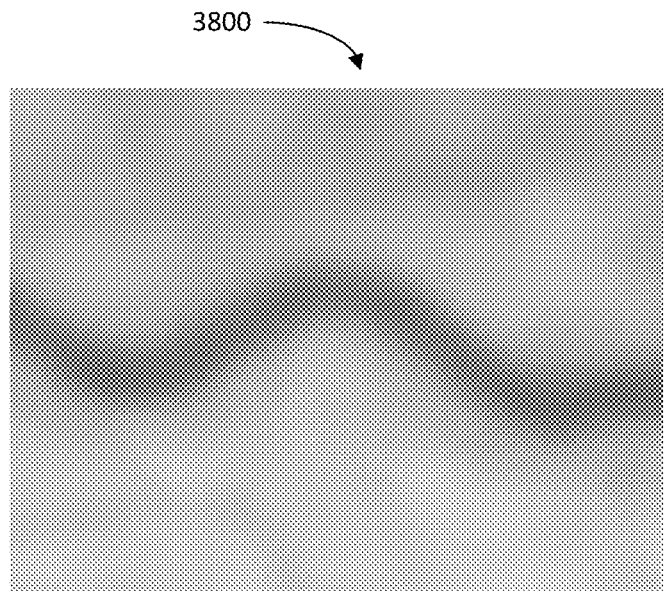
FIG. 38 is the grayscale image of FIG. 37 after normalization.
Figure 39:
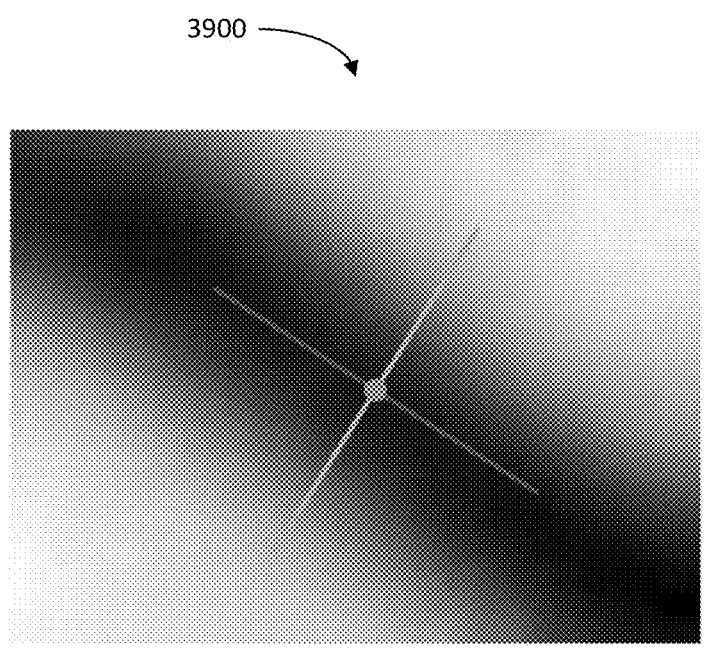
FIG. 39 is a close-up of FIG. 38, with two separate examples of lines used to test for Gaussian similarity
Figure 41:
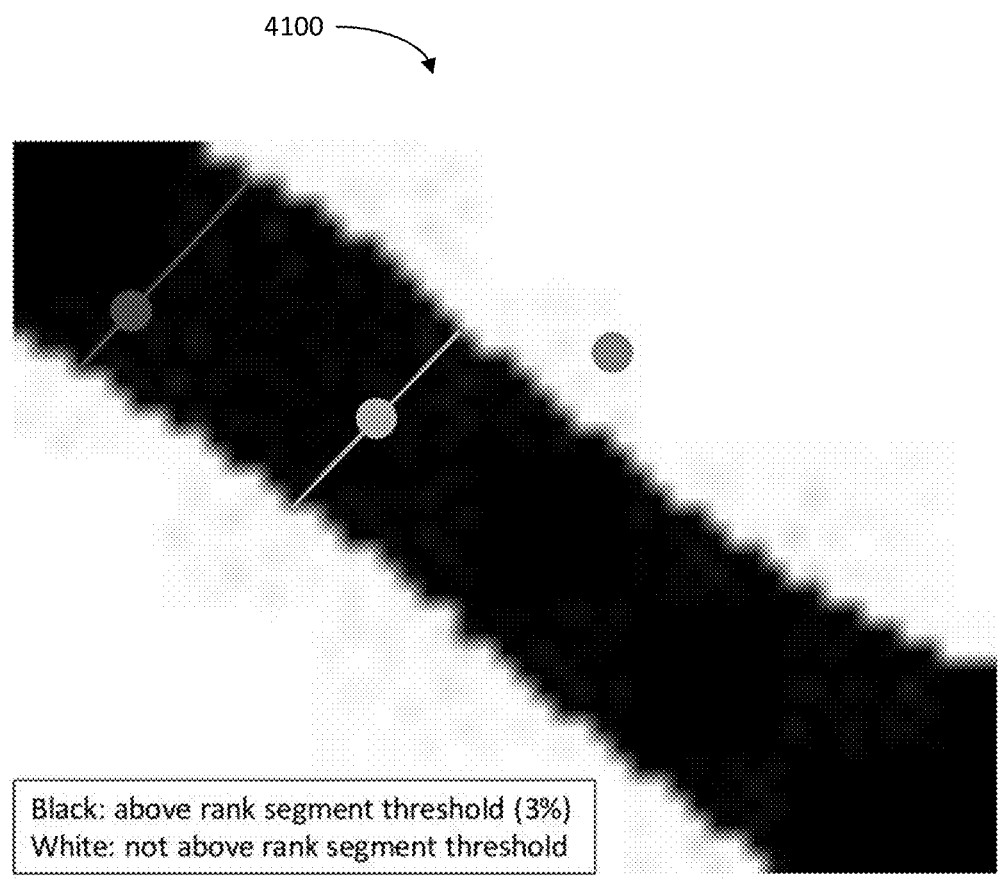
FIG. 41 is a visualization of rank segmented pixels of the image of FIG. 40.

Referring now to FIG. 33, there is shown a diagram 3300 of some steps of a method for image processing useful for the device of FIG. 24. First a color image 3302, shown in FIG. 34, of a patient's eye is captured and stored in a storage. Then, the color image 3302 is converted to a grayscale image 3304, shown in FIG. 35, and stored. Next, a box blur noise reduction filter is applied 3304 to the grayscale image and stored. Then, a box blur noise reduction filter is applied to the stored image and the results are stored. Next, the noise reduced image is normalized. Then, pixels between white (conjunctiva) and black (blood vessel) are increased in range from the normalization and stored. Next, a Gaussian Matched filter is applied to the range increased image and the results are stored. Then, each pixel of the Gaussian Matched image are scored on a likelihood of being in a blood vessel and the results are stored. Next, for each of the scored pixels, the optimal orthogonal angle is calculated and the results are stored. Then, the stored results are rank segmented 3308. Next, the best calculated blood vessel candidates are segmented and stored. Then, a midpoint for each segment is calculated. Next, midpoints 3310 for the rank segmented pixels, shown in FIG. 41, are calculated and stored. Next, blood vessel diameters associated with each midpoint are calculated and the results are stored. Then, each calculated midpoint is chained 3312 to the other calculated midpoints. Next, the chained midpoints are connected to calculate 3312 a line that traverses the blood vessel. Then, a feature analysis is performed on the blood vessel using statistics 3320 and the blood vessel chains to identify and measure features in the microcirculation to calculate diabetic conditions.

Figure 40:
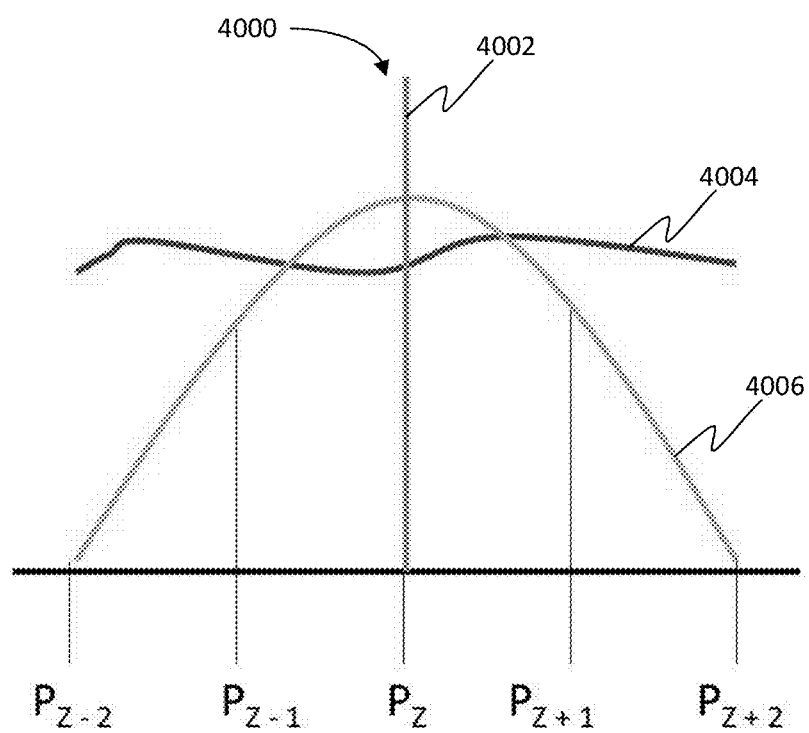
FIG. 40 is a graph of intensity values as a lines move away from a midpoint of the blood vessel in the image of FIG. 39.

For the step of converting the color image to grayscale, only the light intensity, shown in FIG. 40, of each pixel is stored, rather than color data. This decreases amount of image data to process and reduces confounding data. Color is not a necessary component for identifying and measuring features (except for hemosiderin which is done separately). The method converts the color data associated with each pixel to a single measure of light intensity. Although there are multiple methods of calculating the single measure of light intensity value, the preferred conversion uses the following formula:

$$\text{Gray Value} = 0.114B + 0.587G + 0.299R \quad \text{(Eq. 1)}$$

Where: B=blue channel; G=green channel; R=red channel

The step of applying the box blur filter is used to reduce image noise. Image noise reduction reduces the impact of blood vessels located deeper in the conjunctiva and thereby focuses the calculations on superficial and more visible vessels. The box blur filter further comprises the steps of first creating a new image, where each pixel in the new image is equal to the average value of the neighboring pixels in the original image. Neighboring pixels are defined as a box with length k centered on the pixel. The length k can be in the range of 1 to the size of the image. However, in a preferred embodiment, k=5, and the blur is run progressively five times.

The step of normalization increases the dynamic range of the image, exaggerating the difference in pixel intensity between the pixels in a blood vessel and pixels not in a blood vessel. The pixels in the blood vessels will become darker, and the pixels not in the blood vessels will become lighter thereby increasing the image contrast. This step increases the reliability of feature detection algorithms and produce improved results with the increased contrast. Normalization comprises the steps of analyzing each pixel for a white value and a black value. Then, setting the whitest pixel to white, and the darkest pixel to black. Next, scaling all other pixels accordingly using the following formula:

$$\text{pixel}(x,y) = [(\text{pixel}(x,y) - \min)/(\max - \min)] \times 255 \quad \text{(Eq. 2)}$$

Where, pixel(x,y)=an individual pixel; min and max=the smallest and largest value, respectively, in the entire image.

The step of enhancing the image using a Gaussian Matched Filter comprises the steps of: first, for every point P(x,y) in the image, analyze a line of pixels of some length centered on P(x,y). Then, score how closely the pixel intensities match a Gaussian curve, with P(x,y) acting as the mean. Next, repeating the scoring for a number of equidistant radials, centered on P(x,y). In a preferred embodiment, the score is calculated using 12 radials. Then, storing the highest score and the angle that produced the high score for every point in the image. The score represents the likelihood that the pixel is inside a vessel, and the angle represents the angle of the line orthogonal to the blood vessel. Since these scores represent likelihoods, or intensities, they can be easily converted to a grayscale image for illustrative purposes.

The step of rank segmented pixels can be visualized in a graph 4000. The graph 4100 is an example of intensity values that can be expected as the lines move away from the point PZ 4002. The intensity curve 4006 for the radial line 4004 would be relatively flat when all of the pixels are dark. The intensity curve for the radial line 4008 will be similar to a Gaussian curve as the pixels start with high intensity and lessen away from the point PZ 4002. The radial line 4008 will score very well, whereas the dark line 4004 would not score well.

For the steps of midpoint classification and midpoint chaining, the calculated midpoints have little value on their own, and must be connected to the other midpoints in the blood vessel. In a preferred embodiment, the method uses the O'Brien Midpoint Chaining algorithm to chain adjacent midpoints together to create a line that traverses the center of a blood vessel. Adjacent midpoints of the same blood vessel are likely to be the two that are nearest each other and have similar diameters and orthogonal angles. The method further comprises the steps of: for a midpoint $P_A$, identify the midpoint $P_B$ which is closest to $P_A$ but not chained to $P_A$. $P_B$ is the nearest neighbor to $P_A$. If $P_A$ is also the nearest neighbor to $P_B$, and the diameters and orthogonal angles of $P_A$ and $P_B$ are within a threshold, then connect the two as adjacent midpoints. The chain is continued to be built on both ends, until no suitable neighbors exist. Once every midpoint has been examined, if the k longest chains do not contain a determined numbers of points, then the threshold constraints of midpoint diameter and orthogonal angle are slightly eased to build longer chains. In a preferred embodiment, k=3. If any of the longest chains terminate before the edge of the image, then more rank segmented points are added to complete the chain. Because the circulatory system is a closed system, the blood vessels in the eye are most likely to enter and exit the image, rather than abruptly end within it. If a calculated chain ends, it is likely that including more points will allow the completion of the chain.

Midpoint chaining further comprises the steps of providing more rank segmented points to for examination. In a preferred embodiment, the top 5% of midpoints are examined (increased from top 3%). The new points are aware of the points previously chained together. Next, for each new point $P_A$, if $P_A$ passes the O'Brien Midpoint Identification criteria, and $P_A$ is the nearest neighbor to a point ($P_B$) which is chained to only one other point, and $P_B$ is the nearest neighbor to $P_A$, and $P_A$ and $P_B$ have similar diameters and orthogonal angles, then chain together $P_A$ and $P_B$.

The step of feature analysis comprises the steps of first calculating vessel tortuosity. Vessel tortuosity is equal to the curvature of the chain divided by the length of the chain, or the sum of the dot products over the sum of the lengths.

$$\frac{\sum_{i=1}^{n-1} u_i \cdot u_{i+1}}{\sum_{i=1}^{n-1} |u_{i+1} - u_i|} \quad \text{(Eq. 3)}$$

Abnormal Vessel Diameter, Uneven Vessel Thickness: The average, max, min, and variance of diameter for each chain will be calculated, as well as average diameter and variance over all chains. The diameter of a vessel with uneven thickness will significantly deviate from mean, or will have a significantly large range between the max and min values.

The step of feature analysis further comprises the steps of first analyzing chains that terminate at a point not near the edge of the image and identifies them as damaged blood vessels. Then, chains calculated as a damaged vessel, that have significant increase in diameter or circular shape (detected with a Hough transform) at the end of the chain are calculated as a microaneurysm. Next, chains identified as a damaged vessel, that have significant decrease in diameter at the end of the chain are identified as a distended blood vessel. Then, the image is divided into a number of equal size sections and analyzed for abnormal vessel distribution and ischemic sites. An image with an abnormal distribution will have a significant variance in the number of midpoints found amongst the bins. An image with ischemic sites will have bins with no midpoints. Next, the image is analyzed for "Boxcar" blood flow phenomena. A chain with alternating areas of light and dark intensity, or a number of small chains with similar orthogonal angles and diameters that would connect through non-rank segmented pixels. Additionally, the original color image will be examined for significant areas of the yellow-brown color that is characteristic of hemosiderin deposits.

In addition to the above the following embodiments are also contemplated for this invention.

Hardware Options:
Smartphone, macro-lens for magnification, proprietary tube 2404/eyepiece 2402/lighting
Embedded Device (including handheld computer, macro-lens, proprietary tube 2404/eyepiece 2402/lighting)
tablet, slitlamps, CCD cameras, CMOS cameras, SLRs, mirrorless cameras, camcorders, other imaging devices, slitlamp, ophthalmoscope, objective lenses, microscope, chin rest, corneal topographer Feature Set:
abnormal vessel diameter, vessel tortuosity, uneven vessel thickness, damaged vessel, microaneurysm, abnormal vessel distribution, ischemic sites, abnormal Arteriole; Venule ratio, hemosiderin deposits, distended vessel, "boxcar" blood flow phenomena, sickle vessel, blood flow sludging, abnormal blood flow velocity
Corneal topography (mapping the eye), Ocular pressure, Conreal topology, Visual acuity, conjunctival vs. scheral vessels, retinal fundoscopy, pachymetry Image Processing:
Methods for Filtering Images and Identifying Vessels: Topological Skeleton, Sobel Edge Detection, Scharr Operator, Laplacian Operator, Canny Edge Detector, Countour Detection, Convex Hull, Histogram Equalization, Erosion/Dialtion, Top Hat Transform, Green Channel Extraction
Methods for Identifying and Measuring Features:
Tortuosity (method that we will likely use): calculate the variance of the vessel angles
Tortuosity: Sum the absolute values of the differences of vessel angle from one midpoint to the next. Divide this value by the number of midpoints
Tortuosity: Divide the total number of midpoints on the vessel by the distance from the first midpoint to the last midpoint of the vessel
Uneven Vessel Thickness: Sum all of the midpoint diameters of the vessel. Divide this value by the number of midpoints
Uneven Vessel Thickness: Count the number of midpoints with diameters greater than some known value.
Uneven Vessel Thickness: Calculate the distribution of midpoint diameters
Damaged Vessel: Identify a green channel intensity increase from the penultimate midpoint to the final midpoint.
Microaneurysm: Identify an increase in vessel diameter from the penultimate midpoint to the final midpoint.
Distended Vessels: Identify a decrease in vessel diameter from the penultimate midpoint to the final midpoint.
The light source can be composed of a silicon tube 2404 with LED lights inside. The LED's are directed radially out, away from the lens 2702. The silicon tube 2404 directs the light to the eye in a uniform, and diffuse manner. This is done to provide uniform lighting on the surface of the eye, while minimizing the reflected glare. This light source is placed against the patient's face, which also serves to control the lighting by blocking out ambient light.
The target light can be moved to a post 2710 that can rotate 180° around the lens 2702. This allows the patient to focus their eye on a specific location, so the device can capture an image of the conjunctiva. The target light can then be rotated to the other side, to capture an image of the other eye. The target light is placed on the opposite side of the face from the eye being imaged. This causes the eye being imaged to look towards the middle of the face, exposing as much of the conjunctiva as possible for imaging.
The light source can be activated when the fixation light 2708 is rotated.

What has been described is a new and improved a system, method and device for automatic noninvasive screening for diabetes and pre-diabetes, overcoming the limitations and disadvantages inherent in the related art.

Although the present invention has been described with a degree of particularity, it is understood that the present disclosure has been made by way of example and that other versions are possible. As various changes could be made in the above description without departing from the scope of the invention, it is intended that all matter contained in the above description or shown in the accompanying drawings shall be illustrative and not used in a limiting sense. The spirit and scope of the appended claims should not be limited to the description of the preferred versions contained in this disclosure.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. §112.

What is claimed is:

1. A method for an automatic noninvasive screening for diabetes and pre-diabetes using at least one image, the method comprising the steps of:
   a) capturing a color image of a patient's eye;
   b) storing the image in a storage for processing;
   c) converting the color image to a grayscale image;
   d) applying a box blur filter to the grayscale image;
   e) applying a noise reduction filter the box blur image;
   f) normalizing the noise reduced image;
   g) increasing the range in the normalized, noise reduced image between white, identifying conjunctiva, and black, identifying blood vessel, pixels on the normalized image;
   h) applying a Gaussian Matched filter to the range increased image;
   i) scoring each pixel of the Gaussian Matched image on a likelihood of being in a blood vessel;
   j) calculating, for each of the scored pixels, an optimal orthogonal angle;
   k) rank segmenting each of the optimal orthogonal angles;
   l) identifying blood vessel candidates from the segmented rankings using a threshold;
   m) calculating a midpoint for each segmented ranking;
   n) calculating midpoints for each segmented rank;
   o) calculating blood vessel diameters associated with each midpoint;
   p) chaining each identified midpoint to the other identified midpoints;
   q) calculating a line that connects and traverses the blood vessel through the chained midpoints creating a line; and
   r) performing feature analysis on the blood vessel using statistics and the blood vessel chains to identify and measure features in the micro circulation to identified diabetic conditions.

2. The method of claim 1, where the step of normalization increases the dynamic range of the image, exaggerating the difference in pixel intensity between the pixels in a blood vessel and pixels not in a blood vessel.

3. The method of claim 1, where enhancing the image using a Gaussian Matched Filter comprises the steps of:
   a) analyzing, for every point P(x,y), in the image a line of pixels of some length centered on P(x,y);
   b) scoring how closely the pixel intensities match a Gaussian curve, with P(x,y) acting as a mean;
   c) repeating the scoring for a number of equidistant radials, centered on P(x,y); and
   d) storing a highest score and an angle that produced the highest score for every point in the image.

4. The method of claim 1, where the midpoint chaining uses an O'Brien Midpoint Chaining algorithm to chain adjacent midpoints together to create a line that traverses a center of a blood vessel.

5. The method of claim 1, where only a light intensity of each pixel is stored, rather than color data for the step of converting the color image to grayscale.

6. The method of claim 5, where calculating the light intensity of each pixel is done using the formula: Gray Value=0.114B+0.587G+0.299R, where: B=blue channel; G=green channel; R=red channel.

7. The method of claim 1, the image noise is reduced by applying a box blur filter.

8. The method of claim 7, where the box blur filter comprises the steps of:
   a) creating a new image, where each pixel in the new image is equal to the average value of the neighboring pixels in the original image;
   b) defining neighboring pixels as a box with length k centered on the pixel; and
   c) repeating step b) for a number of iterations.

9. The method of claim 8, where the length k is in the range of 1 pixel to the number of pixels in the image.

10. The method of claim 8, where the length k is five pixels.

11. The method of claim 1, where normalization comprises the steps of:
    a) analyzing each pixel for a white value and a black value;
    b) setting the whitest pixel to white, and the darkest pixel to black; and
    c) scaling all other pixels accordingly.

12. The method of claim 11, where the step of scaling uses the formula pixel(x,y)=[(pixel(x,y)−min)I(max−min)]×255, where pixel(x,y)=an individual pixel, where min is a smallest pixel intensity and max is a largest pixel intensity, respectively.

13. The method of claim 12, where the scaling is applied to an entire image, and where min is the smallest pixel intensity and max is the largest pixel intensity, respectively, in the entire image.

14. The method of claim 12, where the image is split into smaller local bins, and where min is the smallest pixel intensity and max is the largest pixel intensity, respectively, in the local bin.

15. The method of claim 3, where the score is calculated using twelve radials.

16. The method of claim 1, where the feature analysis, the method comprising the steps of:
    a) identifying vessel tortuosity;
    b) calculating an average, maximum, minimum, and variance of diameter for each chain to determine abnormal vessel diameter and uneven vessel thickness;
    c) analyzing chains that terminate at a point not near the edge of the image;
    d) identifying terminated chains as damaged blood vessels;
    e) analyzing the chains identified as damaged vessels for a significant increase in diameter, a circular shape or both an increase in diameter and a circular shape at the end of the chain;
    f) identifying the chains of damaged vessels as a microaneurysm;
    g) analyzing chains identified as a damaged vessel for distended blood vessel, where the chains have a significant decrease in diameter at the end of the chain;
    h) identifying the distended blood vessels;
    i) dividing the image into a number of equal size sections;
    j) analyzing the divided image for abnormal vessel distribution;
    k) analyzing the divided image for ischemic sites; and
    l) analyzing the image for "Boxcar" blood flow phenomena.

17. The method of claim 16, where the circular shape is detected with a Hough transform.

18. The method of claim 16 further comprising calculating an average diameter and variance over all chains.

19. The method of claim 16 further comprising the step of analyzing the original color image for significant areas of yellow-brown color indicating hemosiderin deposits.

20. The method of claim 16 further comprises the step of calculating vessel tortuosity.

21. The method of claim 20, where blood vessel tortuosity is calculated as being equal to a curvature of the chain divided by a length of the chain.

22. The method of claim 20, where blood vessel tortuosity is calculated as being equal to a sum of dot products of a sum of lengths.

* * * * *